(12) United States Patent
Fraser et al.

(10) Patent No.: US 7,459,430 B2
(45) Date of Patent: *Dec. 2, 2008

(54) METHODS OF USING ZICONOTIDE TO TREAT OVERACTIVE BLADDER

(75) Inventors: Matthew Oliver Fraser, Apex, NC (US); Karl Bruce Thor, Morrisville, NC (US); Edward C. Burgard, Chapel Hill, NC (US)

(73) Assignee: Dynogen Pharmaceuticals, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/449,489

(22) Filed: Jun. 8, 2006

(65) Prior Publication Data

US 2006/0234939 A1 Oct. 19, 2006

Related U.S. Application Data

(62) Division of application No. 10/796,952, filed on Mar. 10, 2004, now Pat. No. 7,084,116.

(60) Provisional application No. 60/453,171, filed on Mar. 10, 2003.

(51) Int. Cl.
*A61K 38/12* (2006.01)

(52) U.S. Cl. .......................... 514/9; 530/300

(58) Field of Classification Search .............. None
See application file for complete search history.

(56) References Cited

U.S. PATENT DOCUMENTS

| | | | |
|---|---|---|---|
| 5,670,622 A | 9/1997 | Shon et al. | |
| 5,698,549 A | 12/1997 | Steers et al. | |
| 5,739,276 A | 4/1998 | Shon et al. | |
| 6,077,680 A | 6/2000 | Kem et al. | |
| 6,190,691 B1 | 2/2001 | Mak | |
| 7,084,116 B2 * | 8/2006 | Fraser et al. | 514/9 |

FOREIGN PATENT DOCUMENTS

| | | |
|---|---|---|
| EP | 1 042 468 A2 | 10/2000 |
| EP | 1 117 680 A2 | 7/2001 |
| JP | 11035483 | 2/1999 |
| WO | WO 95/23132 | 8/1995 |
| WO | WO 96/33206 | 10/1996 |
| WO | WO 98/23639 | 6/1998 |
| WO | WO 99/28342 | 6/1999 |
| WO | WO 00/18402 | 4/2000 |
| WO | WO 00/18801 | 4/2000 |
| WO | WO 03/018561 A1 | 3/2003 |
| WO | WO 2004/054560 A1 | 7/2004 |

OTHER PUBLICATIONS

Catterall, W.A., "Structure and Regulation of Voltage-Gated $Ca^{2+}$ Channels," *Annu. Rev. Cell Dev. Biol.*, 2000, pp. 521-555, vol. 16.

Guido, M. III, et al., "Clinical Experience with Levetiracetam," *Epilepsia*, 2001, p. 180, vol. 42(7).

Maggi, C.A., et al., "Effect of Omega Conotoxin on Reflex Responses Mediated by Activiation of Capsaicin-Sensitive Nerves of the Rat Urinary Bladder and Peptide Release from the Rat Spinal Cord," *Neuroscience*, 1990, pp. 243-250, vol. 34(1).

\* cited by examiner

*Primary Examiner*—Cecilia Tsang
*Assistant Examiner*—Satyanarayana Gudibande
(74) *Attorney, Agent, or Firm*—Alston & Bird, LLP

(57) ABSTRACT

The invention relates to methods of using Cav2.2 subunit calcium channel modulators to treat painful and non-painful lower urinary tract disorders and the related genitourinary tract disorders vulvodynia and vulvar vestibulitis in normal and spinal cord injured patients.

14 Claims, 3 Drawing Sheets

METHODS OF USING ZICONOTIDE TO TREAT OVERACTIVE BLADDER

CROSS-REFERENCE TO RELATED APPLICATIONS

This application is a divisional of U.S. application Ser. No. 10/796,952, filed Mar. 10, 2004, which claims the benefit of U.S. Provisional Application No. 60/453,171, filed Mar. 10, 2003; which is hereby incorporated by reference.

FIELD OF THE INVENTION

The invention relates to methods of using Cav2.2 subunit calcium channel modulators for treating painful and non-painful lower urinary tract disorders and the related genitourinary tract disorders vulvodynia and vulvar vestibulitis in normal and spinal cord injured patients.

BACKGROUND OF THE INVENTION

Lower urinary tract disorders affect the quality of life of millions of men and women in the United States every year. Disorders of the lower urinary tract include overactive bladder, prostatitis and prostadynia, interstitial cystitis, benign prostatic hyperplasia, and, in spinal cord injured patients, spastic bladder.

Overactive bladder is a treatable medical condition that is estimated to affect 17 to 20 million people in the United States. Current treatments for overactive bladder include medication, diet modification, programs in bladder training, electrical stimulation, and surgery. Currently, antimuscarinics (which are subtypes of the general class of anticholinergics) are the primary medication used for the treatment of overactive bladder. This treatment suffers from limited efficacy and side effects such as dry mouth, dry eyes, dry vagina, palpitations, drowsiness, and constipation, which have proven difficult for some individuals to tolerate.

Prostatitis and prostadynia are other lower urinary tract disorders that have been suggested to affect approximately 2-9% of the adult male population (Collins M M, et al., (1998) *J. Urology*, 159: 1224-1228). Currently, there are no established treatments for prostatitis and prostadynia. Antibiotics are often prescribed, but with little evidence of efficacy. COX-2 selective inhibitors and α-adrenergic blockers and have been suggested as treatments, but their efficacy has not been established. Hot sitz baths and anticholinergic drugs have also been employed to provide some symptomatic relief.

Interstitial cystitis is another lower urinary tract disorder of unknown etiology that predominantly affects young and middle-aged females, although men and children can also be affected. Past treatments for interstitial cystitis have included the administration of antihistamines, sodium pentosanpolysulfate, dimethylsulfoxide, steroids, tricyclic antidepressants and narcotic antagonists, although these methods have generally been unsuccessful (Sant, G. R. (1989) Interstitial cystitis: pathophysiology, clinical evaluation and treatment. *Urology Annal* 3: 171-196).

Benign prostatic hyperplasia (BPH) is a non-malignant enlargement of the prostate that is very common in men over 40 years of age. Invasive treatments for BPH include transurethral resection of the prostate, transurethral incision of the prostate, balloon dilation of the prostate, prostatic stents, microwave therapy, laser prostatectomy, transrectal high-intensity focused ultrasound therapy and transurethral needle ablation of the prostate. However, complications may arise through the use of some of these treatments, including retrograde ejaculation, impotence, postoperative urinary tract infection and some urinary incontinence. Non-invasive treatments for BPH include androgen deprivation therapy and the use of 5α-reductase inhibitors and α-adrenergic blockers. However, these treatments have proven only minimally to moderately effective for some patients.

Lower urinary tract disorders are particularly problematic for individuals suffering from spinal cord injury. Following spinal cord injury, the bladder is usually affected in one of two ways: 1) "spastic" or "reflex" bladder, in which the bladder fills with urine and a reflex automatically triggers the bladder to empty; or 2) "flaccid" or "non-reflex" bladder, in which the reflexes of the bladder muscles are absent or slowed. Treatment options for these disorders usually include intermittent catheterization, indwelling catheterization, or condom catheterization, but these methods are invasive and frequently inconvenient. Urinary sphincter muscles may also be affected by spinal cord injuries, resulting in an inability of urinary sphincter muscles to relax when the bladder contracts ("dyssynergia"). Traditional treatments for dyssynergia include medications that have been somewhat inconsistent in their efficacy or surgery.

In addition to the lower urinary tract disorders described above, the related genitourinary tract disorders vulvodynia and vulvar vestibulitis have been etiologically and pathologically linked to such lower urinary tract disorders as interstitial cystitis (See Selo-Ojeme et al. (2002) *Int. Urogynecol. J Pelvic Floor Dysfunction* 13: 261-2; Metts (2001) *Am. Fam. Physician* 64: 1199-206; Wesselmann (2001) *World J. Urol.* 19: 180-5; Parsons et al. (2001) *Obstet. Gynecol.* 98: 127-32; Heim (2001) *Am. Fam. Physician* 63: 1535-44; Stewart et al. (1997) *J. Reprod. Med.* 42: 131-4; Fitzpatrick et al. (1993) *Obstet. Gynecol.* 81: 860-2). Vulvar vestibulitis syndrome (herein "vulvar vestibulitis") is a subtype of vulvodynia. Vulvodynia is a complex gynecologic syndrome characterized by unexplained vulvar pain, sexual dysfunction, and psychological disability. It has been estimated that 1.5 million American women may suffer from some degree of vulvodynia. Because of their multiple causes, these disorders can be very difficult to treat. The first-line therapy is typically the treatment of suspected causes by pharmacologic treatment of infections and the discontinued use of suspected irritants and therapeutic agents that may contribute to the problem. Topical anesthetics, corticosteroids, and sex hormones may provide some symptomatic relief. Further treatments may include dietary modifications, physical therapy and biofeedback, use of topical, oral, or injected therapeutic agents, or surgery. Unfortunately, no single treatment works in all patients. Moreover, many of these approaches involve complex medical procedures, significant costs, and/or undesirable side effects.

Because existing therapies and treatments for lower urinary tract disorders and the related genitourinary tract disorders vulvodynia and vulvar vestibulitis in normal and spinal cord injured patients are associated with limitations as described above, new therapies and treatments are therefore desirable.

SUMMARY OF THE INVENTION

Compositions and methods for treating painful and non-painful lower urinary tract disorders, and the related genitourinary tract disorders vulvodynia and vulvar vestibulitis in normal and spinal cord injured patients, are provided. Compositions of the invention comprise Cav2.2 subunit calcium channel modulators and other peptide, non-peptide, and peptidomimetic drug-like molecules that bind to Cav2.2-containing calcium channels, as well as pharmaceutically acceptable, pharmacologically active salts, esters, amides, prodrugs, active metabolites, and other derivatives thereof.

The compositions are administered in therapeutically effective amounts to a patient in need thereof for treating painful and non-painful lower urinary tract disorders and the related genitourinary tract disorders vulvodynia and vulvar vestibulitis in normal and spinal cord injured patients. It is recognized that the compositions may be administered by any means of administration as long as an effective amount for the treatment of painful and non-painful symptoms associated with lower urinary tract disorders and the related genitourinary tract disorders vulvodynia and vulvar vestibulitis in normal and spinal cord injured patients is delivered. The compositions may be formulated, for example, for sustained, continuous, or as-needed administration.

BRIEF DESCRIPTION OF THE DRAWINGS

FIG. 1 depicts intermicturition intervals before (Sal) and after (remaining groups) bladder hyperactivity caused by continuous intravesical dilute acetic acid infusion. ω-Conotoxin MVIIA was administered intrathecally at increasing doses, and data is represented as Mean (±SEM) intermicturition intervals in minutes.

FIG. 2 depicts bladder capacity before (Sal) and after (remaining groups) bladder hyperactivity caused by continuous intravesical dilute acetic acid infusion. ω-Conotoxin MVIIA was administered intrathecally at increasing doses and data has been normalized to irritation control values (AA/Veh3) and is represented as Mean (±SEM).

FIG. 3.

DETAILED DESCRIPTION OF THE INVENTION

Overview and Definitions

Figure 1:
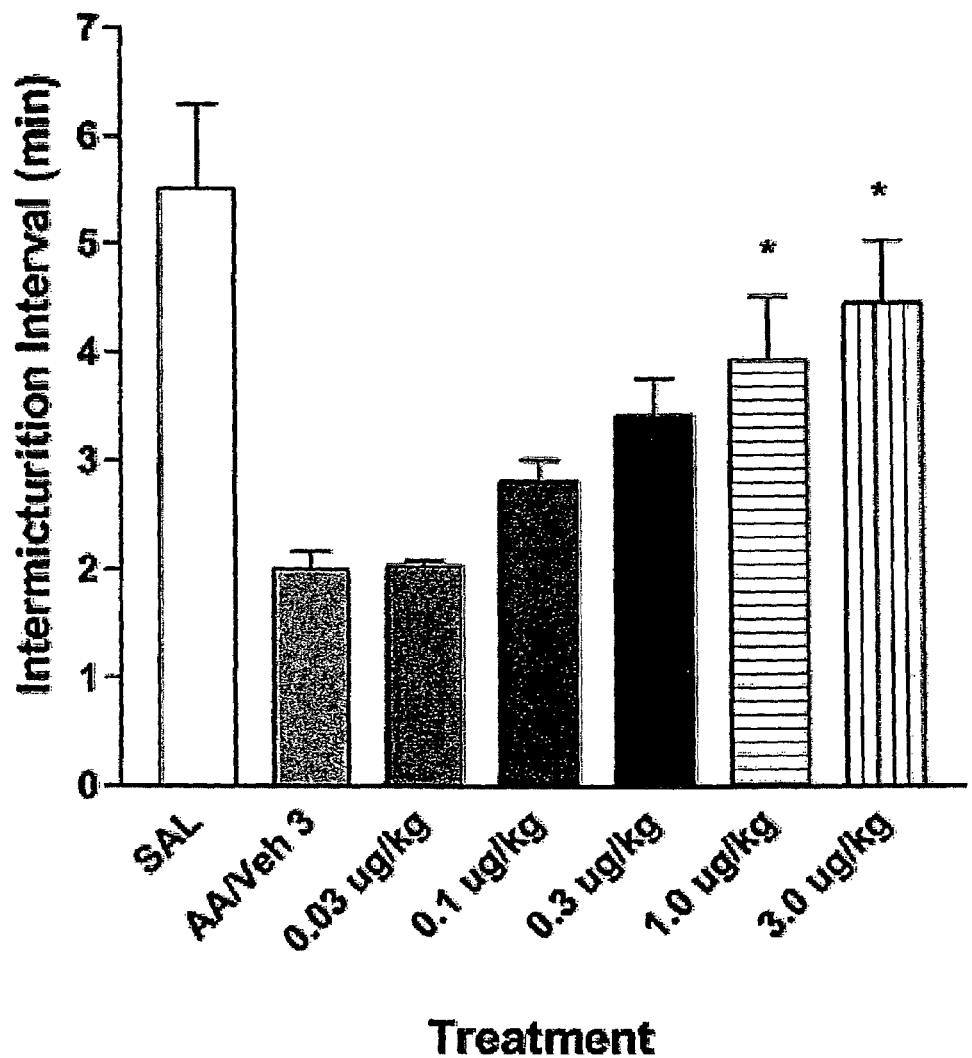
FIG. 1.

The present invention provides compositions and methods for treating painful and non-painful lower urinary tract disorders and the related genitourinary tract disorders vulvodynia and vulvar vestibulitis in normal and spinal cord injured patients. The lower urinary tract disorders of the present invention include, but are not limited to such disorders as painful and non-painful overactive bladder, prostatitis and prostadynia, interstitial cystitis, benign prostatic hyperplasia, and, in spinal cord injured patients, and spastic bladder. The compositions comprise a therapeutically effective dose of a Cav2.2 subunit calcium channel modulator. The methods are accomplished by administering, for example, various compositions and formulations that contain quantities of a Cav2.2 subunit calcium channel modulator and other peptide, non-peptide, and peptidomimetic drug-like molecules that bind to Cav2.2-containing calcium channels.

Before describing the present invention in detail, it is to be understood that this invention is not limited to specific active agents, dosage forms, dosing regimens, or the like, as such may vary. It is also to be understood that the terminology used herein is for the purpose of describing particular embodiments only, and is not intended to be limiting.

It must be noted that as used in this specification and the appended embodiments, the singular forms "a," "an," and "the" include plural referents unless the context clearly dictates otherwise. Thus, for example, reference to "an active agent" or "a pharmacologically active agent" includes a single active agent as well as two or more different active agents in combination, reference to "a carrier" includes mixtures of two or more carriers as well as a single carrier, and the like.

By "non-painful" is intended sensations or symptoms including mild or general discomfort that a patient subjectively describes as not producing or resulting in pain.

By "painful" is intended sensations or symptoms that a patient subjectively describes as producing or resulting in pain.

By "lower urinary tract" is intended all parts of the urinary system except the kidneys. By "lower urinary tract disorder" is intended any disorder involving the lower urinary tract, including but not limited to overactive bladder, prostatitis, interstitial cystitis, benign prostatic hyperplasia, and spastic and flaccid bladder. By "non-painful lower urinary tract disorder" is intended any lower urinary tract disorder involving sensations or symptoms, including mild or general discomfort, that a patient subjectively describes as not producing or resulting in pain. By "painful lower urinary tract disorder" is intended any lower urinary tract disorder involving sensations or symptoms that a patient subjectively describes as producing or resulting in pain.

By "bladder disorder" is intended any condition involving the urinary bladder. By "non-painful bladder disorder" is intended any bladder disorder involving sensations or symptoms, including mild or general discomfort, that a patient subjectively describes as not producing or resulting in pain. By "painful bladder disorder" is intended any bladder disorder involving sensations or symptoms that a patient subjectively describes as producing or resulting in pain.

By "overactive bladder" is intended any form of lower urinary tract disorder characterized by increased frequency of micturition or the desire to void, whether complete or episodic, and where loss of voluntary control ranges from partial to total and whether there is loss of urine (incontinence) or not. By "painful overactive bladder" is intended any form of overactive bladder, as defined above, involving sensations or symptoms that a patient subjectively describes as producing or resulting in pain. By "non-painful overactive bladder" is intended any form of overactive bladder, as defined above, involving sensations or symptoms, including mild or general discomfort, that a patient subjectively describes as not producing or resulting in pain. Non-painful symptoms can include, but are not limited to, urinary urgency, incontinence, urge incontinence, stress incontinence, urinary frequency, and nocturia.

"OAB wet" is used herein to describe overactive bladder in patients with incontinence, while "OAB dry" is used herein to describe overactive bladder in patients without incontinence.

By "urinary urgency" is intended sudden strong urges to urinate with little or no chance to postpone the urination. By "incontinence" is meant the inability to control excretory functions, including urination (urinary incontinence). By "urge incontinence" or "urinary urge incontinence" is intended the involuntary loss of urine associated with an abrupt and strong desire to void. By "stress incontinence" or "urinary stress incontinence" is intended a medical condition in which urine leaks when a person coughs, sneezes, laughs, exercises, lifts heavy objects, or does anything that puts pressure on the bladder. By "urinary frequency" is intended urinating more frequently than the patient desires. As there is considerable interpersonal variation in the number of times in a day that an individual would normally expect to urinate, "more frequently than the patient desires" is further defined as a greater number of times per day than that patient's historical baseline. "Historical baseline" is further defined as the median number of times the patient urinated per day during a normal or desirable time period. By "nocturia" is intended being awakened from sleep to urinate more frequently than the patient desires.

By "neurogenic bladder" or "neurogenic overactive bladder" is intended overactive bladder as described further herein that occurs as the result of neurological damage due to disorders including but not limited to stroke, Parkinson's disease, diabetes, multiple sclerosis, peripheral neuropathy, or spinal cord lesions.

By "detrusor hyperreflexia" is intended a condition characterized by uninhibited detrusor, wherein the patient has some sort of neurologic impairment. By "detrusor instability" or "unstable detrusor" is intended conditions where there is no neurologic abnormality.

By "prostatitis" is intended any type of disorder associated with an inflammation of the prostate, including chronic bacterial prostatitis and chronic non-bacterial prostatitis. By "non-painful prostatitis" is intended prostatitis involving sensations or symptoms, including mild or general discomfort, that a patient subjectively describes as not producing or resulting in pain. By "painful prostatitis" is intended prostatitis involving sensations or symptoms that a patient subjectively describes as producing or resulting in pain.

"Chronic bacterial prostatitis" is used in its conventional sense to refer to a disorder associated with symptoms that include inflammation of the prostate and positive bacterial cultures of urine and prostatic secretions. "Chronic non-bacterial prostatitis" is used in its conventional sense to refer to a disorder associated with symptoms that include inflammation of the prostate and negative bacterial cultures of urine and prostatic secretions. "Prostadynia" is used in its conventional sense to refer to a disorder generally associated with painful symptoms of chronic non-bacterial prostatitis as defined above, without inflammation of the prostate. "Interstitial cystitis" is used in its conventional sense to refer to a disorder associated with symptoms that include irritative voiding symptoms, urinary frequency, urgency, nocturia, and suprapubic or pelvic pain related to and relieved by voiding.

"Benign prostatic hyperplasia" is used in its conventional sense to refer to a disorder associated with benign enlargement of the prostate gland.

"Spastic bladder" or "reflex bladder" is used in its conventional sense to refer to a condition following spinal cord injury in which bladder emptying has become unpredictable.

"Flaccid bladder" or "non-reflex bladder" is used in its conventional sense to refer to a condition following spinal cord injury in which the reflexes of the bladder muscles are absent or slowed.

"Dyssynergia" is used in its conventional sense to refer to a condition following spinal cord injury in which patients characterized by an inability of urinary sphincter muscles to relax when the bladder contracts.

"Vulvodynia" is used in its conventional sense to refer to a condition characterized by gynecologic syndrome characterized by unexplained vulvar pain, sexual dysfunction, and psychological disability.

"Vulvar vestibulitis" (also known as "vulvar vestibulitis syndrome," "focal vulvitis," and "vestibular adenitis") is used in its conventional sense to refer to a condition that is a subtype of vulvodynia characterized by: 1) pain on vestibular touch or attempted vaginal entry; 2) tenderness to Q-tip pressure localized within the vulvar vestibule; 3) physical findings confined to vestibular erythema of various degrees; and 4) an exclusion of other causes for vestibular erythema and tenderness, such as candidiasis (yeast infections) or herpes infections. Other symptoms may include itching, swelling and excoriation.

The terms "active agent" and "pharmacologically active agent" are used interchangeably herein to refer to a chemical compound that induces a desired effect, i.e., in this case, treatment of painful and non-painful lower urinary tract disorders, and the related genitourinary tract disorders vulvodynia and vulvar vestibulitis, in normal and spinal cord injured patients. The primary active agents herein are compounds that modulate Cav2.2 calcium channel subunits. In addition, a combination therapy wherein a compound that modulates Cav2.2 calcium channel subunits is administered with one or more additional active agents is also within the scope of the present invention. Such combination therapy may be carried out by administration of the different active agents in a single composition, by concurrent administration of the different active agents in different compositions, or by sequential administration of the different active agents. Included are derivatives and analogs of those compounds or classes of compounds specifically mentioned that also induce the desired effect.

The term "Cav2.2 subunit calcium channel modulator" as used herein is intended an agent that is capable of binding to the Cav2.2 subunit of a calcium channel to produce a physiological effect, such as opening, closing, blocking, up-regulating expression, or down-regulating expression of the channel. Unless otherwise indicated, the term "Cav2.2 subunit calcium channel modulator" is intended to include amino acid compounds, peptide, nonpeptide, peptidomimetic, small molecular weight organic compounds, and other compounds that modulate or interact with the Cav2.2 subunit of a calcium channel (e.g., a binding event) or proteins associated with the Cav2.2 subunit of a calcium channel (e.g., a binding event) such as anchor proteins, as well as salts, esters, amides, prodrugs, active metabolites, and other derivatives thereof. Further, it is understood that any salts, esters, amides, prodrugs, active metabolites or other derivatives are pharmaceutically acceptable as well as pharmacologically active.

The term "peptidomimetic" is used in its conventional sense to refer to a molecule that mimics the biological activity of a peptide but is no longer peptidic in chemical nature, including molecules that lack amide bonds between amino acids, as well as pseudo-peptides, semi-peptides and peptoids. Peptidomimetics according to this invention provide a spatial arrangement of reactive chemical moieties that closely resembles the three-dimensional arrangement of active groups in the peptide on which the peptidomimetic is based. As a result of this similar active-site geometry, the peptidomimetic has effects on biological systems that are similar to the biological activity of the peptide.

The terms "treating" and "treatment" as used herein refer to relieving the painful or non-painful symptoms or other clinically observed sequelae for clinically diagnosed disorders as described herein, including disorders associated with lower urinary tract, and the related genitourinary tract disorders vulvodynia and vulvar vestibulitis, in normal and spinal cord injured patients.

By an "effective" amount or a "therapeutically effective amount" of a drug or pharmacologically active agent is meant a nontoxic but sufficient amount of the drug or agent to provide the desired effect, i.e., relieving the painful and non-painful symptoms associated with lower urinary tract disorders, and the related genitourinary tract disorders vulvodynia and vulvar vestibulitis, in normal and spinal cord injured patients, as explained above. It is recognized that the effective amount of a drug or pharmacologically active agent will vary depending on the route of administration, the selected compound, and the species to which the drug or pharmacologically active agent is administered. It is also recognized that one of skill in the art will determine appropriate effective amounts by taking into account such factors as metabolism, bioavailability, and other factors that affect plasma levels of a drug or pharmacologically active agent following administration within the unit dose ranges disclosed further herein for different routes of administration.

By "pharmaceutically acceptable," such as in the recitation of a "pharmaceutically acceptable carrier," or a "pharmaceutically acceptable acid addition salt," is meant a material that is not biologically or otherwise undesirable, i.e., the material may be incorporated into a pharmaceutical composition administered to a patient without causing any undesirable biological effects or interacting in a deleterious manner with any of the other components of the composition in which it is contained. "Pharmacologically active" (or simply "active") as in a "pharmacologically active" derivative or metabolite, refers to a derivative or metabolite having the same type of pharmacological activity as the parent compound. When the term "pharmaceutically acceptable" is used to refer to a derivative (e.g., a salt or an analog) of an active agent, it is to be understood that the compound is pharmacologically active as well, i.e., therapeutically effective for treating painful and non-painful lower urinary tract disorders, and the related genitourinary tract disorders vulvodynia and vulvar vestibulitis, in normal and spinal cord injured patients.

By "continuous" dosing is meant the chronic administration of a selected active agent. By "as-needed" dosing, also known as "pro re nata" "prn" dosing, and "on demand" dosing or administration is meant the administration of a single dose of the active agent at some time prior to commencement of an activity wherein suppression of the painful and non-painful symptoms of a lower urinary tract disorder, and the related genitourinary tract disorders vulvodynia and vulvar vestibulitis, in normal and spinal cord injured patients, would be desirable. Administration can be immediately prior to such an activity, including about 0 minutes, about 10 minutes, about 20 minutes, about 30 minutes, about 1 hour, about 2 hours, about 3 hours, about 4 hours, about 5 hours, about 6 hours, about 7 hours, about 8 hours, about 9 hours, or about 10 hours prior to such an activity, depending on the formulation.

By "short-term" is intended any period of time up to and including about 8 hours, about 7 hours, about 6 hours, about 5 hours, about 4 hours, about 3 hours, about 2 hours, about 1 hour, about 40 minutes, about 20 minutes, or about 10 minutes after drug administration.

By "rapid-offset" is intended any period of time up to and including about 8 hours, about 7 hours, about 6 hours, about 5 hours, about 4 hours, about 3 hours, about 2 hours, about 1 hour, about 40 minutes, about 20 minutes, or about 10 minutes after drug administration.

The term "controlled release" is intended to refer to any drug-containing formulation in which release of the drug is not immediate, i.e., with a "controlled release" formulation, oral administration does not result in immediate release of the drug into an absorption pool. The term is used interchangeably with "non-immediate release" as defined in Remington: The Science and Practice of Pharmacy, Twentieth Ed. (Philadelphia, Pa.: Lippincott Williams & Wilkins, 2000).

The "absorption pool" represents a solution of the drug administered at a particular absorption site, and $k_r$, $k_a$, and $k_e$ are first-order rate constants for: 1) release of the drug from the formulation; 2) absorption; and 3) elimination, respectively. For immediate release dosage forms, the rate constant for drug release $k_r$ is far greater than the absorption rate constant $k_a$. For controlled release formulations, the opposite is true, i.e., $k_r \ll k_a$, such that the rate of release of drug from the dosage form is the rate-limiting step in the delivery of the drug to the target area. The term "controlled release" as used herein includes any nonimmediate release formulation, including but not limited to sustained release, delayed release and pulsatile release formulations.

The term "sustained release" is used in its conventional sense to refer to a drug formulation that provides for gradual release of a drug over an extended period of time, and that preferably, although not necessarily, results in substantially constant blood levels of a drug over an extended time period such as up to about 72 hours, about 66 hours, about 60 hours, about 54 hours, about 48 hours, about 42 hours, about 36 hours, about 30 hours, about 24 hours, about 18 hours, about 12 hours, about 10 hours, about 8 hours, about 7 hours, about 6 hours, about 5 hours, about 4 hours, about 3 hours, about 2 hours, or about 1 hour after drug administration.

The term "delayed release" is used in its conventional sense to refer to a drug formulation that provides for an initial release of the drug after some delay following drug administration and that preferably, although not necessarily, includes a delay of up to about 10 minutes, about 20 minutes, about 30 minutes, about 1 hour, about 2 hours, about 3 hours, about 4 hours, about 5 hours, about 6 hours, about 7 hours, about 8 hours, about 9 hours, about 10 hours, about 11 hours, or about 12 hours.

The term "pulsatile release" is used in its conventional sense to refer to a drug formulation that provides release of the drug in such a way as to produce pulsed plasma profiles of the drug after drug administration. The term "immediate release" is used in its conventional sense to refer to a drug formulation that provides for release of the drug immediately after drug administration.

The term "immediate release" is used in its conventional sense to refer to a drug formulation that provides for release of the drug immediately after drug administration.

By the term "transdermal" drug delivery is meant delivery by passage of a drug through the skin or mucosal tissue and into the bloodstream.

The term "topical administration" is used in its conventional sense to mean delivery of a topical drug or pharmacologically active agent to the skin or mucosa.

The term "oral administration" is used in its conventional sense to mean delivery of a drug through the mouth and ingestion through the stomach and digestive tract.

The term "inhalation administration" is used in its conventional sense to mean delivery of an aerosolized form of the drug by passage through the nose or mouth during inhalation and passage of the drug through the walls of the lungs.

The term "intravesical administration" is used in its conventional sense to mean delivery of a drug directly into the bladder.

By the term "parenteral" drug delivery is meant delivery by passage of a drug into the blood stream without first having to pass through the alimentary canal, or digestive tract. Parenteral drug delivery may be "subcutaneous," referring to delivery of a drug by administration under the skin. Another form of parenteral drug delivery is "intramuscular," referring to delivery of a drug by administration into muscle tissue. Another form of parenteral drug delivery is "intradermal," referring to delivery of a drug by administration into the skin. An additional form of parenteral drug delivery is "intravenous," referring to delivery of a drug by administration into a vein. An additional form of parenteral drug delivery is "intraarterial," referring to delivery of a drug by administration into an artery. Another form of parenteral drug delivery is "transdermal," referring to delivery of a drug by passage of the drug through the skin and into the bloodstream. Another form of parenteral drug delivery is "intrathecal," referring to delivery of a drug directly into the into the intrathecal space (where fluid flows around the spinal cord).

Still another form of parenteral drug delivery is "transmucosal," referring to administration of a drug to the mucosal surface of an individual so that the drug passes through the mucosal tissue and into the individual's blood stream. Transmucosal drug delivery may be "buccal" or "transbuccal," referring to delivery of a drug by passage through an individual's buccal mucosa and into the bloodstream. Another form of transmucosal drug delivery herein is "lingual" drug delivery, which refers to delivery of a drug by passage of a drug through an individual's lingual mucosa and into the bloodstream. Another form of transmucosal drug delivery herein is "sublingual" drug delivery, which refers to delivery of a drug by passage of a drug through an individual's sublingual mucosa and into the bloodstream. Another form of transmucosal drug delivery is "nasal" or "intranasal" drug delivery, referring to delivery of a drug through an individual's nasal mucosa and into the bloodstream. An additional form of transmucosal drug delivery herein is "rectal" or "transrectal" drug delivery, referring to delivery of a drug by passage of a drug through an individual's rectal mucosa and into the bloodstream. Another form of transmucosal drug delivery is "urethral" or "transurethral" delivery, referring to delivery of the drug into the urethra such that the drug contacts and passes through the wall of the urethra. An additional form of transmucosal drug delivery is "vaginal" or "transvaginal" delivery, referring to delivery of a drug by passage of a drug through an individual's vaginal mucosa and into the bloodstream. An additional form of transmucosal drug delivery is "perivaginal" delivery, referring to delivery of a drug through the vaginolabial tissue into the bloodstream.

In order to carry out the method of the invention, a selected active agent is administered to a patient suffering from a painful or non-painful lower urinary tract disorder, and the related genitourinary tract disorders vulvodynia and vulvar vestibulitis, in normal and spinal cord injured patients. A therapeutically effective amount of the active agent may be administered orally, intravenously, subcutaneously, transmucosally (including buccally, sublingually, transurethrally, and rectally), topically, transdermally, by inhalation, intravesically, intrathecally or using any other route of administration.

Lower Urinary Tract Disorders

Lower urinary tract disorders affect the quality of life of millions of men and women in the United States every year. While the kidneys filter blood and produce urine, the lower urinary tract is concerned with storage and elimination of this waste liquid and includes all other parts of the urinary tract except the kidneys. Generally, the lower urinary tract includes the ureters, the urinary bladder, and the urethra. Disorders of the lower urinary tract include painful and non-painful overactive bladder, prostatitis and prostadynia, interstitial cystitis, benign prostatic hyperplasia, and, in spinal cord injured patients, spastic bladder and flaccid bladder.

Overactive bladder is a treatable medical condition that is estimated to affect 17 to 20 million people in the United States. Symptoms of overactive bladder include urinary frequency, urgency, nocturia (the disturbance of nighttime sleep because of the need to urinate) and urge incontinence (accidental loss of urine) due to a sudden and unstoppable need to urinate. As opposed to stress incontinence, in which loss of urine is associated with physical actions such as coughing, sneezing, exercising, or the like, urge incontinence is usually associated with an overactive detrusor muscle (the smooth muscle of the bladder which contracts and causes it to empty).

There is no single etiology for overactive bladder. Neurogenic overactive bladder (or neurogenic bladder) occurs as the result of neurological damage due to disorders such as stroke, Parkinson's disease, diabetes, multiple sclerosis, peripheral neuropathy, or spinal cord lesions. In these cases, the overactivity of the detrusor muscle is termed detrusor hyperreflexia. By contrast, non-neurogenic overactive bladder can result from non-neurological abnormalities including bladder stones, muscle disease, urinary tract infection or drug side effects.

Due to the enormous complexity of micturition (the act of urination) the exact mechanism causing overactive bladder is unknown. Overactive bladder may result from hypersensitivity of sensory neurons of the urinary bladder, arising from various factors including inflammatory conditions, hormonal imbalances, and prostate hypertrophy. Destruction of the sensory nerve fibers, either from a crushing injury to the sacral region of the spinal cord, or from a disease that causes damage to the dorsal root fibers as they enter the spinal cord may also lead to overactive bladder. In addition, damage to the spinal cord or brain stem causing interruption of transmitted signals may lead to abnormalities in micturition. Therefore, both peripheral and central mechanisms may be involved in mediating the altered activity in overactive bladder.

In spite of the uncertainty regarding whether central or peripheral mechanisms, or both, are involved in overactive bladder, many proposed mechanisms implicate neurons and pathways that mediate non-painful visceral sensation. Pain is the perception of an aversive or unpleasant sensation and may arise through a variety of proposed mechanisms. These mechanisms include activation of specialized sensory receptors that provide information about tissue damage (nociceptive pain), or through nerve damage from diseases such as diabetes, trauma or toxic doses of drugs (neuropathic pain) (See, e.g., A. I. Basbaum and T. M. Jessell (2000) The perception of pain. In *Principles of Neural Science,* 4th. ed.; Benevento et al. (2002) *Physical Therapy Journal* 82:601-12). Nociception may give rise to pain, but not all stimuli that activate nociceptors are experienced as pain (A. I. Basbaum and T. M. Jessell (2000) The perception of pain. In *Principles of Neural Science,* 4th. ed.). Somatosensory information from the bladder is relayed by nociceptive Aδ and C fibers that enter the spinal cord via the dorsal root ganglion (DRG) and project to the brainstem and thalamus via second or third order neurons (Andersson (2002) *Urology* 59:18-24; Andersson (2002) *Urology* 59:43-50; Morrison, J., Steers, W. D., Brading, A., Blok, B., Fry, C., de Groat, W. C., Kakizaki, H., Levin, R., and Thor, K. B., "Basic Urological Sciences" In: Incontinence (vol. 2) Abrams, P. Khoury, S., and Wein, A. (Eds.) Health Publications, Ltd., Plymbridge Ditributors, Ltd., Plymouth, UK., (2002). A number of different subtypes of sensory afferent neurons may be involved in neurotransmission from the lower urinary tract. These may be classified as, but not limited to, small diameter, medium diameter, large diameter, myelinated, unmyelinated, sacral, lumbar, peptidergic, non-peptidergic, IB4 positive, IB4 negative, C fiber, Aδ fiber, high threshold or low threshold neurons. Nociceptive input to the DRG is thought to be conveyed to the brain along several ascending pathways, including the spinothalamic, spinoreticular, spinomesencephalic, spinocervical, and in some cases dorsal column/medial lemniscal tracts (A. I. Basbaum and T. M. Jessell (2000) The perception of pain. In *Principles of Neural Science,* 4th. ed.). Central mechanisms, which are not fully understood, are thought to convert some, but not all, nociceptive information into painful sensory perception (A. I. Basbaum and T. M. Jessell (2000) The perception of pain. In *Principles of Neural Science,* 4th. ed.). Although many compounds have been explored as treatments for disorders involving pain of the bladder or other pelvic visceral organs, relatively little work has been directed toward treatment of non-painful sensory symptoms associated with bladder disorders such as overactive bladder.

The compounds of the present invention are useful in the treatment of both painful and non-painful overactive bladder. Current treatments for overactive bladder include medication, diet modification, programs in bladder training, electrical stimulation, and surgery. Currently, antimuscarinics (which are subtypes of the general class of anticholinergics) are the primary medication used for the treatment of overactive bladder. This treatment suffers from limited efficacy and side effects such as dry mouth, dry eyes, dry vagina, palpitations, drowsiness, and constipation, which have proven difficult for some individuals to tolerate. Therefore, the compounds of the present invention meet an existing need for new treatments for both painful and non-painful overactive bladder.

Overactive bladder (or OAB) can occur with or without incontinence. In recent years, it has been recognized among those of skill in the art that the cardinal symptom of OAB is urgency without regard to any demonstrable loss of urine. For example, a recent study examined the impact of all OAB symptoms on the quality of life of a community-based sample of the United States population. (Liberman et al. (2001) *Urology* 57: 1044-1050). This study demonstrated that individuals suffering from OAB without any demonstrable loss of urine have an impaired quality of life when compared with controls. Additionally, individuals with urgency alone have an impaired quality of life compared with controls.

Although urgency is now believed to be the primary symptom of OAB, to date it has not been evaluated in a quantified way in clinical studies. Corresponding to this new understanding of OAB, however, the terms OAB Wet (with incontinence) and OAB Dry (without incontinence) have been proposed to describe these different patient populations (see, e.g., WO03/051354). The prevalence of OAB Wet and OAB Dry is reported to be similar in men and women, with a prevalence rate in the United States of 16.6% (Stewart et al., "Prevalence of Overactive Bladder in the United States: Results from the NOBLE Program," Abstract Presented at the Second International Consultation on Incontinence, July 2001, Paris, France). In particular, the compounds of the present invention are useful in the treatment of OAB Wet and OAB Dry.

Prostatitis and prostadynia are other lower urinary tract disorders that have been suggested to affect approximately 2-9% of the adult male population (Collins M M, et al., (1998) "How common is prostatitis? A national survey of physician visits," *Journal of Urology,* 159: 1224-1228). Prostatitis is associated with an inflammation of the prostate, and may be subdivided into chronic bacterial prostatitis and chronic non-bacterial prostatitis. Chronic bacterial prostatitis is thought to arise from bacterial infection and is generally associated with such symptoms as inflammation of the prostate, the presence of white blood cells in prostatic fluid, and/or pain. Chronic non-bacterial prostatitis is an inflammatory and painful condition of unknown etiology characterized by excessive inflammatory cells in prostatic secretions despite a lack of documented urinary tract infections, and negative bacterial cultures of urine and prostatic secretions. Prostadynia (chronic pelvic pain syndrome) is a condition associated with the painful symptoms of chronic non-bacterial prostatitis without an inflammation of the prostate.

The compounds of the present invention are useful for the treatment of prostatitis and prostadynia. Currently, there are no established treatments for prostatitis and prostadynia. Antibiotics are often prescribed, but with little evidence of efficacy. COX-2 selective inhibitors and $\alpha$-adrenergic blockers and have been suggested as treatments, but their efficacy has not been established. Hot sitz baths and anticholinergic drugs have also been employed to provide some symptomatic relief. Therefore, the compounds of the present invention meet an existing need for new treatments for prostatitis and prostadynia.

Interstitial cystitis is another lower urinary tract disorder of unknown etiology that predominantly affects young and middle-aged females, although men and children can also be affected. Symptoms of interstitial cystitis may include irritative voiding symptoms, urinary frequency, urgency, nocturia and suprapubic or pelvic pain related to and relieved by voiding. Many interstitial cystitis patients also experience headaches as well as gastrointestinal and skin problems. In some extreme cases, interstitial cystitis may also be associated with ulcers or scars of the bladder.

The compounds of the present invention are useful for the treatment of interstitial cystitis. Past treatments for interstitial cystitis have included the administration of antihistamines, sodium pentosanpolysulfate, dimethylsulfoxide, steroids, tricyclic antidepressants and narcotic antagonists, although these methods have generally been unsuccessful (Sant, G. R. (1989) Interstitial cystitis: pathophysiology, clinical evaluation and treatment. *Urology Annal* 3: 171-196). Therefore, the compounds of the present invention meet an existing need for new treatments for interstitial cystitis.

Benign prostatic hyperplasia (BPH) is a non-malignant enlargement of the prostate that is very common in men over 40 years of age. BPH is thought to be due to excessive cellular growth of both glandular and stromal elements of the prostate. Symptoms of BPH include urinary frequency, urge incontinence, nocturia, and reduced urinary force and speed of flow.

The compounds of the present invention are useful for the treatment of BPH. Invasive treatments for BPH include transurethral resection of the prostate, transurethral incision of the prostate, balloon dilation of the prostate, prostatic stents, microwave therapy, laser prostatectomy, transrectal high-intensity focused ultrasound therapy and transurethral needle ablation of the prostate. However, complications may arise through the use of some of these treatments, including retrograde ejaculation, impotence, postoperative urinary tract infection and some urinary incontinence. Non-invasive treatments for BPH include androgen deprivation therapy and the use of $5\alpha$-reductase inhibitors and $\alpha$-adrenergic blockers. However, these treatments have proven only minimally to moderately effective for some patients. Therefore, the compounds of the present invention meet an existing need for new treatments for BPH.

The compounds of the present invention are also useful for treating lower urinary tract disorders in spinal cord injured patients. After spinal cord injury, the kidneys continue to make urine, and urine can continue to flow through the ureters and urethra because they are the subject of involuntary neural and muscular control, with the exception of conditions where bladder to smooth muscle urethra dyssenergia is present. By contrast, bladder and sphincter muscles are also subject to voluntary neural and muscular control, meaning that descending input from the brain through the spinal cord drives bladder and sphincter muscles to completely empty the bladder. Following spinal cord injury, such descending input may be disrupted such that individuals may no longer have voluntary control of their bladder and sphincter muscles. Spinal cord injuries can also disrupt sensory signals that ascend to the brain, preventing such individuals from being able to feel the urge to urinate when their bladder is full.

Following spinal cord injury, the bladder is usually affected in one of two ways. The first is a condition called "spastic" or "reflex" bladder, in which the bladder fills with urine and a reflex automatically triggers the bladder to empty. This usually occurs when the injury is above the T12 level. Individuals with spastic bladder are unable to determine when, or if, the bladder will empty. The second is "flaccid" or "non-reflex" bladder, in which the reflexes of the bladder muscles are absent or slowed. This usually occurs when the injury is below the T12/L1 level. Individuals with flaccid bladder may experience over-distended or stretched bladders and "reflux" of urine through the ureters into the kidneys. Treatment options for these disorders usually include intermittent catheterization, indwelling catheterization, or condom catheterization, but these methods are invasive and frequently inconvenient. Therefore, the compounds of the present invention meet an existing need for new treatments for spastic bladder and flaccid bladder.

Urinary sphincter muscles may also be affected by spinal cord injuries, resulting in a condition known as "dyssynergia." Dyssynergia involves an inability of urinary sphincter muscles to relax when the bladder contracts, including active contraction in response to bladder contraction, which prevents urine from flowing through the urethra and results in the incomplete emptying of the bladder and "reflux" of urine into the kidneys. Traditional treatments for dyssynergia include medications that have been somewhat inconsistent in their efficacy or surgery. Therefore, the compounds of the present invention meet an existing need for new treatments for dyssynergia.

Peripheral vs. Central Effects

The mammalian nervous system comprises a central nervous system (CNS, comprising the brain and spinal cord) and a peripheral nervous system (PNS, comprising sympathetic, parasympathetic, sensory, motor, and enteric neurons outside of the brain and spinal cord). Where an active agent according to the present invention is intended to act centrally (i.e., exert its effects via action on neurons in the CNS), the active agent must either be administered directly into the CNS or be capable of bypassing or crossing the blood-brain barrier. The blood-brain barrier is a capillary wall structure that effectively screens out all but selected categories of substances present in the blood, preventing their passage into the CNS. The unique morphologic characteristics of the brain capillaries that make up the blood-brain barrier are: 1) epithelial-like high resistance tight junctions which literally cement all endothelia of brain capillaries together within the blood-brain barrier regions of the CNS; and 2) scanty pinocytosis or transendothelial channels, which are abundant in endothelia of peripheral organs. Due to the unique characteristics of the blood-brain barrier, many hydrophilic drugs and peptides that readily gain access to other tissues in the body are barred from entry into the brain or their rates of entry are very low.

The blood-brain barrier can be bypassed effectively by direct infusion of the active agent into the brain, or by intranasal administration or inhalation of formulations suitable for uptake and retrograde transport of the active agent by olfactory neurons.

The most common procedure for administration directly into the CNS is the implantation of a catheter into the ventricular system or intrathecal space. Alternatively, the active agent can be modified to enhance its transport across the blood-brain barrier. This generally requires some solubility of the drug in lipids, or other appropriate modification known to one of skill in the art. For example, the active agent may be truncated, derivatized, latentiated (converted from a hydrophilic drug into a lipid-soluble drug), conjugated to a lipophilic moiety or to a substance that is actively transported across the blood-brain barrier, or modified using standard means known to those skilled in the art. See, for example, Pardridge, Endocrine Reviews 7: 314-330 (1986) and U.S. Pat. No. 4,801,575.

Where an active agent according to the present invention is intended to act exclusively peripherally (i.e., exert its effects via action either on neurons in the PNS or directly on target tissues), it may be desirable to modify the compounds of the present invention such that they will not pass the blood-brain barrier. The principle of blood-brain barrier permeability can therefore be used to design active agents with selective potency for peripheral targets. Generally, a lipid-insoluble drug will not cross the blood-brain barrier, and will not produce effects on the CNS. A basic drug that acts on the nervous system may be altered to produce a selective peripheral effect by quaternization of the drug, which decreases its lipid solubility and makes it virtually unavailable for transfer to the CNS. For example, the charged antimuscarinic drug methscopalamine bromide has peripheral effects while the uncharged antimuscarinic drug scopolamine acts centrally. One of skill in the art can select and modify active agents of the present invention using well-known standard chemical synthetic techniques to add a lipid impermeable functional group such a quaternary amine, sulfate, carboxylate, phosphate, or sulfonium to prevent transport across the blood-brain barrier. Such modifications are by no means the only way in which active agents of the present invention may be modified to be impermeable to the blood-brain barrier; other well known pharmaceutical techniques exist and would be considered to fall within the scope of the present invention.

Agents

Compounds useful in the present invention include any active agent as defined elsewhere herein. Such active agents include, for example, any compound that binds to the Cav2.2 subunit of a calcium channel.

Voltage gated calcium channels, also known as voltage dependent calcium channels, are multi-subunit membrane-spanning proteins which permit controlled calcium influx from an extracellular environment into the interior of a cell. Opening and closing (gating) of voltage gated calcium channels is controlled by a voltage sensitive region of the protein containing charged amino acids that move within an electric field. The movement of these charged groups leads to conformational changes in the structure of the channel resulting in conducting (open/activated) or non-conducting (closed/inactivated) states.

Voltage gated calcium channels are present in a variety of tissues and are implicated in several vital processes in animals. Changes in calcium influx into cells mediated through these calcium channels have been implicated in various human diseases such as epilepsy, stroke, brain trauma, Alzheimer's disease, multi-infarct dementia, other classes of dementia, Korsakoff's disease, neuropathy caused by a viral infection of the brain or spinal cord (e.g., human immunodeficiency viruses, etc.), amyotrophic lateral sclerosis, convulsions, seizures, Huntington's disease, amnesia, or damage to the nervous system resulting from reduced oxygen supply, poison, or other toxic substances (See, e.g., U.S. Pat. No. 5,312,928).

Voltage gated calcium channels have been classified by their electrophysiological and pharmacological properties as T, L, N, P and Q types (for reviews see McCleskey et al. (1991) Curr. Topics Membr. 39:295-326; and Dunlap et al. (1995) Trends. Neurosci. 18:89-98). Because there is some overlap in the biophysical properties of the high voltage-activated channels, pharmacological profiles are useful to further distinguish them. L-type channels are sensitive to dihydropyridine agonists and antagonists. N-type channels are blocked by the peptides ω-conotoxin GVIA and ω-conotoxin MVIIA, peptide toxins from the cone shell mollusks, *Conus geographus* and *Conus magus*, respectively. P-type channels are blocked by the peptide ω-agatoxin IVA from the venom of the funnel web spider, *Agelenopsis aperta*, although some studies have suggested that ω-agatoxin IVA also blocks N-type channels (Sidach at al. (2000) *J. Neurosci.* 20: 7174-82). A fourth type of high voltage-activated calcium channel (Q-type) has been described, although whether the Q- and P-type channels are distinct molecular entities is controversial (Sather et al. (1995) *Neuron* 11:291-303; Stea et al. (1994) *Proc. Natl. Acad. Sci. USA* 91:10576-10580; Bourinet et al. (1999) *Nature Neuroscience* 2:407-415).

Different types of calcium channels are primarily defined by different subunits that may be divided into three structurally and functionally related families: $Ca_v1$, $Ca_v2$, and $Ca_v3$ (for reviews, see Caterall (2000) *Annu. Rev. Cell. Dev. Biol.* 16: 521-55; Ertel et al. (2000) *Neuron* 25: 533-55). L-type currents are mediated by a $Ca_v1$ family of $\alpha_1$ subunits (see Caterall, *Annu. Rev. Cell. Dev. Biol.*, supra). $Ca_v2$ channels form a distinct family with less than 40% amino acid sequence identity with $Ca_v1\alpha_1$ subunits (see Caterall, *Annu. Rev. Cell. Dev. Biol.*, supra). Cloned $Ca_v2.1$ subunits conduct P- or Q-type currents that are inhibited by ω-agatoxin IVA (see Caterall, *Annu. Rev. Cell. Dev. Biol.*, supra; Sather et al. (1993) *Neuron* 11: 291-303; Stea et al. (1994) *Proc. Natl. Acad. Sci. USA* 91: 10576-80; Bourinet et al. (1999) *Nat. Neurosci.* 2: 407-15). $Ca_v2.2$ subunits conduct N-type calcium currents and have a high affinity for ω-conotoxin GVIA, ω-conotoxin MVIIA, and synthetic versions of these peptides including Ziconotide (SNX-111) (see Caterall, *Annu. Rev. Cell. Dev. Biol.*, supra; Dubel et al. (1992) *Proc. Natl. Acad. Sci. USA* 89:5058-62; Williams et al. (1992) *Science* 257: 389-95). Cloned $Ca_v2.3$ subunits conduct a calcium current known as R-type and are resistant to organic antagonists specific for L-type calcium currents and peptide toxins specific for N-type or P/Q-type currents ((see Caterall, *Annu. Rev. Cell. Dev. Biol.*, supra; Randall et al. (1995) *J. Neurosci.* 15: 2995-3012; Soong et al. (1994) *Science* 260: 1133-36; Zhang et al. (1993) *Neuropharmacology* 32: 1075-88).

Agents useful in the practice of the invention include, but are not limited to:

a. ω-conotoxin GVIA or a salt, enantiomer, analog, ester, amide, prodrug, active metabolite, or derivative thereof;

b. ω-conotoxin MVIIA or a salt, enantiomer, analog, ester, amide, prodrug, active metabolite, or derivative thereof;

c. ω-conotoxin CNVIIA or a salt, enantiomer, analog, ester, amide, prodrug, active metabolite, or derivative thereof;

d. ω-conotoxin CVIID or a salt, enantiomer, analog, ester, amide, prodrug, active metabolite, or derivative thereof;

e. ω-conotoxin AM336 or a salt, enantiomer, analog, ester, amide, prodrug, active metabolite, or derivative thereof;

f. Cilnidipine or a salt, enantiomer, analog, ester, amide, prodrug, active metabolite, or derivative thereof;

g. Amlodipine or a salt, enantiomer, analog, ester, amide, prodrug, active metabolite, or derivative thereof;

h. L-cysteine derivative 2A or a salt, enantiomer, analog, ester, amide, prodrug, active metabolite, or derivative thereof;

i. ω-agatoxin IVA or a salt, enantiomer, analog, ester, amide, prodrug, active metabolite, or derivative thereof;

j. N,N-dialkyl-dipeptidylamines or a salt, enantiomer, analog, ester, amide, prodrug, active metabolite, or derivative thereof;

k. Levetiracetam or a salt, enantiomer, analog, ester, amide, prodrug, active metabolite, or derivative thereof; and l. Ziconotide (SNX-111) or a salt, enantiomer, analog, ester, amide, prodrug, active metabolite, or derivative thereof;

m. (S)-alpha-ethyl-2-oxo-1-pyrrolidineacetamide (illustrated below) and disclosed in U.S. Pat. Nos. 4,943,639, 4,837,223, and 4,696,943, or a salt, enantiomer, analog, ester, amide, prodrug, active metabolite, or derivative, thereof;

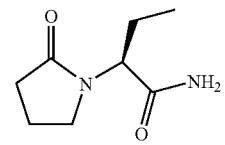

n. Substituted peptidylamines (illustrated below) as disclosed in PCT Publication No. WO 98/54123, or a salt, enantiomer, analog, ester, amide, prodrug, active metabolite, or derivative, thereof,

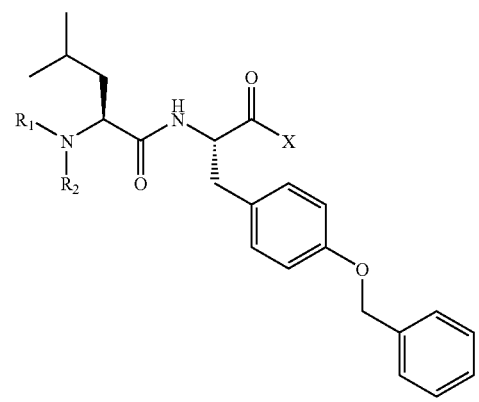

wherein X is selected from the group consisting of OR, $NR_1R_2$, and $COOR_1$, and $R_1$ and $R_2$ are selected from the group consisting of hydrogen and $C_1$-$C_8$ alkyl, aryl, and heteroaryl optimally substituted with one to three substituents;

o. PD-173212 (illustrated below), or a salt, enantiomer, analog, ester, amide, prodrug, active metabolite, or derivative, thereof;

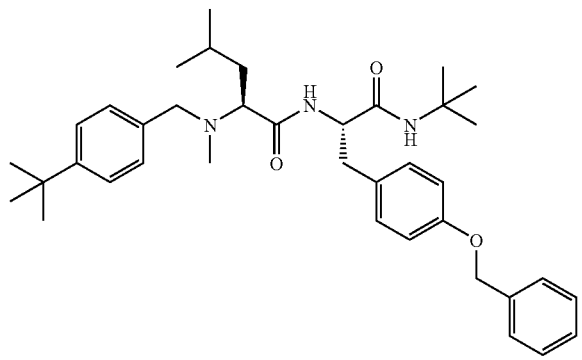

p. Reduced dipeptide analogues (illustrated below) as disclosed in U.S. Pat. No. 6,316,440 and PCT Publication No. WO 00/06559, or a salt, enantiomer, analog, ester, amide, prodrug, active metabolite, or derivative, thereof,

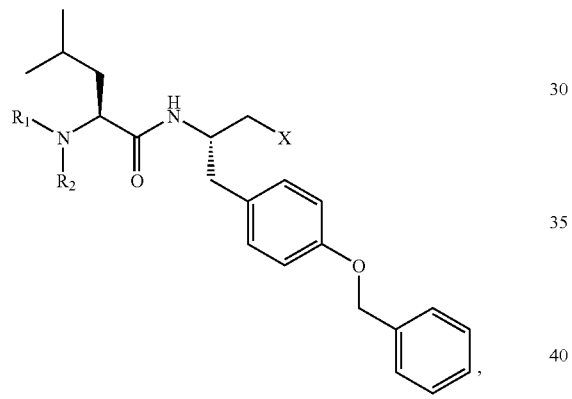

wherein X is selected from the group consisting of OR, $NR_1R_2$, and $COOR_1$, and $R_1$ and $R_2$ are selected from the group consisting of hydrogen and $C_1$-$C_8$ alkyl, aryl, and heteroaryl optimally substituted with one to three substituents, in particular, the two specific embodiments illustrated below;

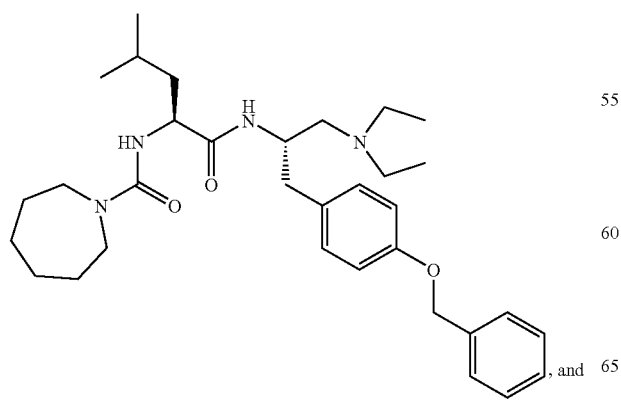

, and

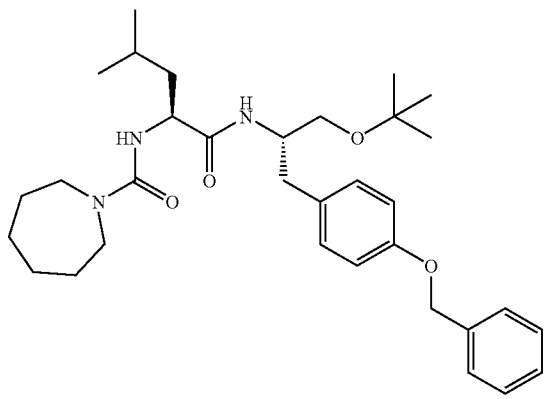

q. Amino acid derivatives (illustrated below) as disclosed in PCT Publication No. WO 99/02146, or a salt, enantiomer, analog, ester, amide, prodrug, active metabolite, or derivative, thereof,

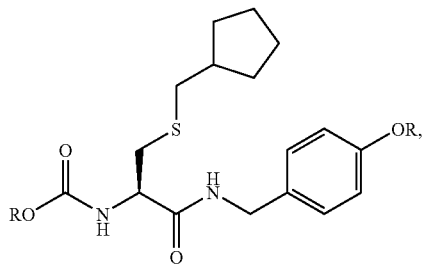

wherein R is selected from the group consisting of hydrogen and $C_1$-$C_6$ alkyl, aryl, and heteroaryl optimally substituted with one to three substituents, in particular, the specific embodiment illustrated below;

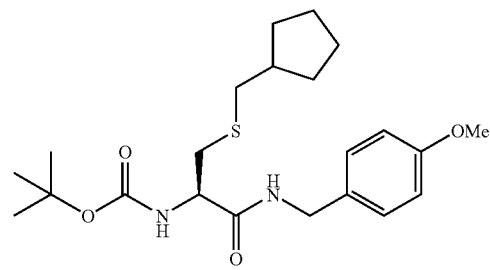

r. Benzazepine derivatives (illustrated below) as disclosed in Japanese Publication No. JP 2002363163, or a salt, enantiomer, analog, ester, amide, prodrug, active metabolite, or derivative, thereof,

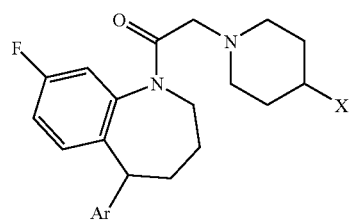

wherein Ar is selected from the group consisting of aryl and heteroaryl optimally substituted with one to three substituents, and X is selected from the group consisting of hydrogen and $C_1$-$C_6$ alkyl and alkoxy, in particular, the specific embodiment illustrated below;

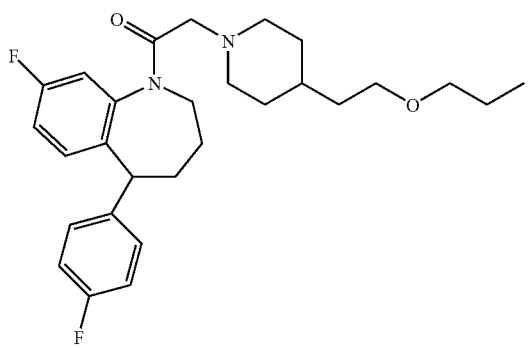

s. Compounds according to the structure illustrated below as disclosed in PCT Publication No. WO 02/36567, or a salt, enantiomer, analog, ester, amide, prodrug, active metabolite, or derivative, thereof,

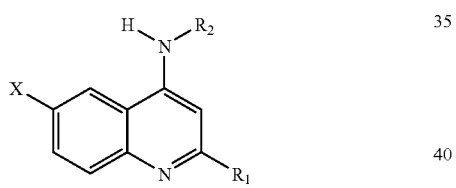

wherein X is selected from the group consisting of $R_1$ and $NHR_1$, $R_1$ is selected from the group consisting of hydrogen and $C_1$-$C_6$ alkyl, aryl, and heteroaryl optimally substituted with one to three substituents, and $R_2$ is $C_1$-$C_4$ alkyl or alkoxy, in particular, the two specific embodiments illustrated below;

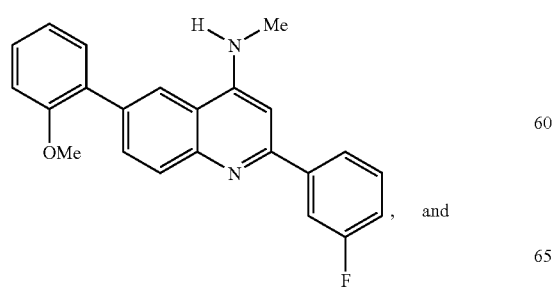

, and

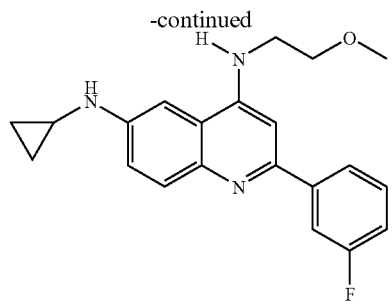

t. Compounds according to the structure illustrated below as disclosed in PCT Publication No. WO 03/018561, or a salt, enantiomer, analog, ester, amide, prodrug, active metabolite, or derivative, thereof, wherein X is selected from the group consisting of hydrogen and halogen, and R is selected from the group consisting of $C_1$-$C_6$ alkyl, aryl, and heteroaryl optimally substituted with one to three substituents, in particular, the two specific embodiments illustrated below;

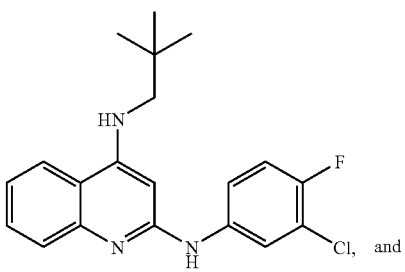

, and

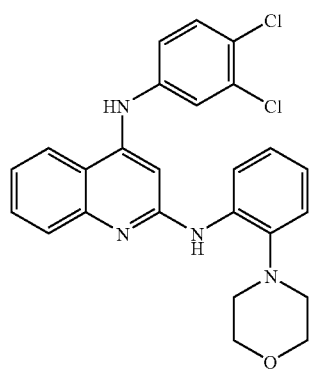

u. Compounds according to the structure illustrated below as disclosed in U.S. Patent Publication No. 2004009991 and PCT Publication No. WO 02/22588, or a salt, enantiomer, analog, ester, amide, prodrug, active metabolite, or derivative, thereof;

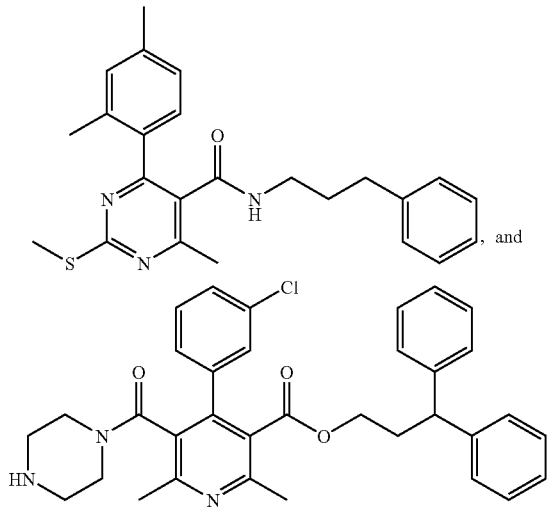
, and v. Dihydropyridine derivatives (illustrated below) as disclosed in U.S. Pat. No. 6,610,717, U.S. Patent Publication No. 2002193605, and PCT Publication No. WO 00/78720, or a salt, enantiomer, analog, ester, amide, prodrug, active metabolite, or derivative, thereof,

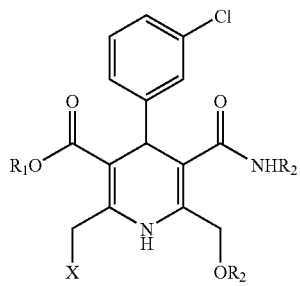

wherein X is selected from the group consisting of hydrogen and $C_1$-$C_4$ alkyl and alkoxy, $R_1$ is selected from the group consisting of hydrogen and $C_1$-$C_4$ alkyl, and $R_2$ is selected from the group consisting of $C_1$-$C_6$ alkyl, alkoxy, alkylamino, and aryl-substituted alkyl, in particular, the two specific embodiments illustrated below; and

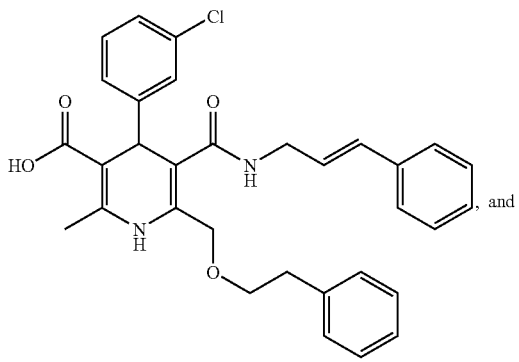
, and

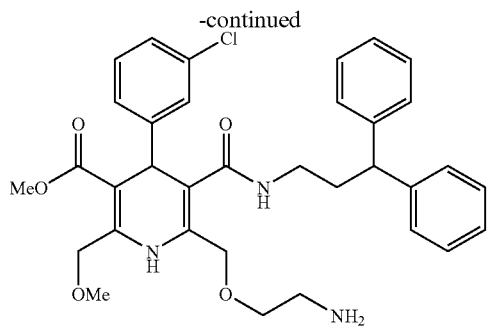

w. Diarylalkene and diarylalkane derivatives (illustrated below) as disclosed in PCT Publication No. WO 03/018538, or a salt, enantiomer, analog, ester, amide, prodrug, active metabolite, or derivative, thereof,

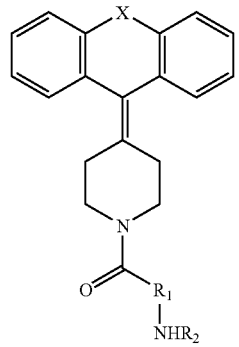

wherein X is selected from the group consisting of CHCH, $CH_2CH_2$, $CH_2$—Y, O, and S, Y is selected from the group consisting of O and S, $R_1$ is selected from the group consisting of $C_1$-$C_4$ alkyl and alkoxy, and $R_2$ is selected from the group consisting of hydrogen, $COOR_1$, and $C_1$-$C_4$ alkyl and alkoxy, in particular, the two specific embodiments illustrated below,

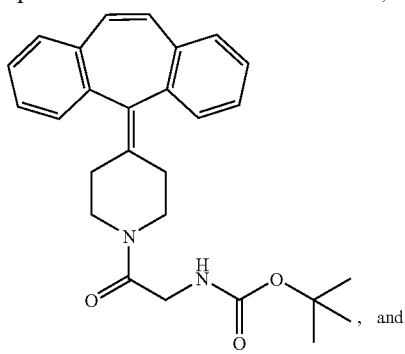
, and

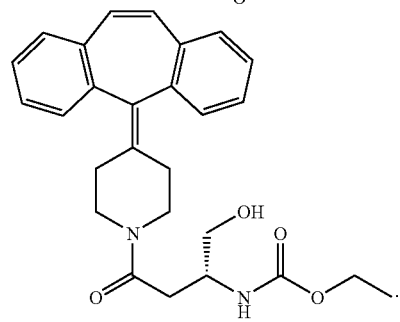

Such active agents also include other peptide, non-peptide, and peptidomimetic drug-like molecules that bind to Cav2.2-containing calcium channels as disclosed in Lewis et al. (2000) J. Biol. Chem. 10: 35335-44; Smith et al. (2002) Pain 96: 119-27; Takahara et al. (2002) Eur. J. Pharmacol. 434: 43-7; Favreau et al. (2001) Biochemistry, 40: 14567-575; Seko et al. (2001) Bioorg. Med. Chem. Lett. 11: 2067-70; Hu et al. (2000) Bioorg. Med. Chem. Lett. 8: 1203-12; Lew et al. (1997) J. Biol. Chem. 272: 12014-23. It is understood that the present invention also encompasses any pharmaceutically acceptable, pharmacologically active salts, enantiomers, analogs, esters, amides, prodrugs, active metabolites, and derivatives of the aforementioned compounds.

The identification of other agents that have affinity for the Cav2.2 subunit of a calcium channel and would be useful in the present invention can be determined by performing Cav2.2 subunit binding affinity, electrophysiolgic, and/or other screening methods as described in Feng et al. (J. Biol. Chem., 278: 20171-20178, 2003), Feng et al. (J. Biol. Chem., 276: 15728-15735, 2001), Favreau et al. (Biochemistry, 40: 14567-575, 2001), and/or U.S. Pat. No. 6,387,897 assigned to NeuroMed Technologies Inc.

Formulations

Formulations of the present invention may include, but are not limited to, continuous, as needed, short-term, rapid-offset, controlled release, sustained release, delayed release, and pulsatile release formulations.

One or more additional active agents can be administered with a Cav2.2 subunit calcium channel modulator either simultaneously or sequentially. The additional active agent will generally, although not necessarily, be one that is effective in treating painful and non-painful lower urinary tract disorders and the related genitourinary tract disorders vulvodynia and vulvar vestibulitis, in normal and spinal cord injured patients, and/or an agent that potentiates the effect of the Cav2.2 subunit calcium channel modulator. Suitable secondary agents include but are not limited to, for example, duloxetine, monoamine reuptake inhibitors, spasmolytics, anticholinergics, and/or any agent that does not inhibit the action of the Cav2.2 subunit calcium channel modulator.

Any of the active agents may be administered in the form of a salt, ester, amide, prodrug, active metabolite, derivative, or the like, provided that the salt, ester, amide, prodrug or derivative is suitable pharmacologically, i.e., effective in the present method. Salts, esters, amides, prodrugs and other derivatives of the active agents may be prepared using standard procedures known to those skilled in the art of synthetic organic chemistry and described, for example, by J. March, Advanced Organic Chemistry: Reactions, Mechanisms and Structure, 4th Ed. (New York: Wiley-Interscience, 1992). For example, acid addition salts are prepared from the free base using conventional methodology, and involves reaction with a suitable acid. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Particularly preferred acid addition salts of the active agents herein are salts prepared with organic acids. Conversely, preparation of basic salts of acid moieties which may be present on an active agent are prepared in a similar manner using a pharmaceutically acceptable base such as sodium hydroxide, potassium hydroxide, ammonium hydroxide, calcium hydroxide, trimethylamine, or the like.

Preparation of esters involves functionalization of hydroxyl and/or carboxyl groups that may be present within the molecular structure of the drug. The esters are typically acyl-substituted derivatives of free alcohol groups, i.e., moieties that are derived from carboxylic acids of the formula RCOOH where R is alkyl, and preferably is lower alkyl. Esters can be reconverted to the free acids, if desired, by using conventional hydrogenolysis or hydrolysis procedures. Amides and prodrugs may also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine. Prodrugs are typically prepared by covalent attachment of a moiety, which results in a compound that is therapeutically inactive until modified by an individual's metabolic system.

Other derivatives and analogs of the active agents may be prepared using standard techniques known to those skilled in the art of synthetic organic chemistry, or may be deduced by reference to the pertinent literature. In addition, chiral active agents may be in isomerically pure form, or they may be administered as a racemic mixture of isomers.

Pharmaceutical Compositions and Dosage Forms

Suitable compositions and dosage forms include tablets, capsules, caplets, pills, gel caps, troches, dispersions, suspensions, solutions, syrups, transdermal patches, gels, powders, magmas, lozenges, creams, pastes, plasters, lotions, discs, suppositories, liquid sprays for nasal or oral administration, dry powder or aerosolized formulations for inhalation, compositions and formulations for intravesical administration, ointments, liquid formulations, pessaries, tampons, foams and the like. Further, those of ordinary skill in the art can readily deduce that suitable formulations involving these compositions and dosage forms, including those formulations as described elsewhere herein.

Oral Dosage Forms

Oral dosage forms include tablets, capsules, caplets, solutions, suspensions and/or syrups, and may also comprise a plurality of granules, beads, powders or pellets that may or may not be encapsulated. Such dosage forms are prepared using conventional methods known to those in the field of pharmaceutical formulation and described in the pertinent texts, e.g., in Remington: The Science and Practice of Pharmacy, supra). Tablets and capsules represent the most convenient oral dosage forms, in which case solid pharmaceutical carriers are employed.

Tablets may be manufactured using standard tablet processing procedures and equipment. One method for forming tablets is by direct compression of a powdered, crystalline or granular composition containing the active agent(s), alone or in combination with one or more carriers, additives, or the like. As an alternative to direct compression, tablets can be prepared using wet-granulation or dry-granulation processes. Tablets may also be molded rather than compressed, starting with a moist or otherwise tractable material; however, compression and granulation techniques are preferred.

In addition to the active agent(s), then, tablets prepared for oral administration using the method of the invention will generally contain other materials such as binders, diluents, lubricants, disintegrants, fillers, stabilizers, surfactants, preservatives, coloring agents, flavoring agents and the like. Binders are used to impart cohesive qualities to a tablet, and thus ensure that the tablet remains intact after compression. Suitable binder materials include, but are not limited to, starch (including corn starch and pregelatinized starch), gelatin, sugars (including sucrose, glucose, dextrose and lactose), polyethylene glycol, propylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, ethyl cellulose, hydroxyethyl cellulose, and the like), and Veegum. Diluents are typically necessary to increase bulk so that a practical size tablet is ultimately provided. Suitable diluents include dicalcium phosphate, calcium sulfate, lactose, cellulose, kaolin, mannitol, sodium chloride, dry starch and powdered sugar. Lubricants are used to facilitate tablet manufacture; examples of suitable lubricants include, for example, vegetable oils such as peanut oil, cottonseed oil, sesame oil, olive oil, corn oil, and oil of theobroma, glycerin, magnesium stearate, calcium stearate, and stearic acid. Stearates, if present, preferably represent at no more than approximately 2 wt. % of the drug-containing core. Disintegrants are used to facilitate disintegration of the tablet, and are generally starches, clays, celluloses, algins, gums or crosslinked polymers. Fillers include, for example, materials such as silicon dioxide, titanium dioxide, alumina, talc, kaolin, powdered cellulose and microcrystalline cellulose, as well as soluble materials such as mannitol, urea, sucrose, lactose, dextrose, sodium chloride and sorbitol. Stabilizers are used to inhibit or retard drug decomposition reactions that include, by way of example, oxidative reactions. Surfactants may be anionic, cationic, amphoteric or nonionic surface active agents.

The dosage form may also be a capsule, in which case the active agent-containing composition may be encapsulated in the form of a liquid or solid (including particulates such as granules, beads, powders or pellets). Suitable capsules may be either hard or soft, and are generally made of gelatin, starch, or a cellulosic material, with gelatin capsules preferred. Two-piece hard gelatin capsules are preferably sealed, such as with gelatin bands or the like. (See, for e.g., Remington: The Science and Practice of Pharmacy, supra), which describes materials and methods for preparing encapsulated pharmaceuticals. If the active agent-containing composition is present within the capsule in liquid form, a liquid carrier is necessary to dissolve the active agent(s). The carrier must be compatible with the capsule material and all components of the pharmaceutical composition, and must be suitable for ingestion.

Solid dosage forms, whether tablets, capsules, caplets, or particulates, may, if desired, be coated so as to provide for delayed release. Dosage forms with delayed release coatings may be manufactured using standard coating procedures and equipment. Such procedures are known to those skilled in the art and described in the pertinent texts (See, for e.g., Remington: The Science and Practice of Pharmacy, supra). Generally, after preparation of the solid dosage form, a delayed release coating composition is applied using a coating pan, an airless spray technique, fluidized bed coating equipment, or the like. Delayed release coating compositions comprise a polymeric material, e.g., cellulose butyrate phthalate, cellulose hydrogen phthalate, cellulose proprionate phthalate, polyvinyl acetate phthalate, cellulose acetate phthalate, cellulose acetate trimellitate, hydroxypropyl methylcellulose phthalate, hydroxypropyl methylcellulose acetate, dioxypropyl methylcellulose succinate, carboxymethyl ethylcellulose, hydroxypropyl methylcellulose acetate succinate, polymers and copolymers formed from acrylic acid, methacrylic acid, and/or esters thereof.

Sustained release dosage forms provide for drug release over an extended time period, and may or may not be delayed release. Generally, as will be appreciated by those of ordinary skill in the art, sustained release dosage forms are formulated by dispersing a drug within a matrix of a gradually bioerodible (hydrolyzable) material such as an insoluble plastic, a hydrophilic polymer, or a fatty compound, or by coating a solid, drug-containing dosage form with such a material. Insoluble plastic matrices may be comprised of, for example, polyvinyl chloride or polyethylene. Hydrophilic polymers useful for providing a sustained release coating or matrix cellulosic polymers include, without limitation: cellulosic polymers such as hydroxypropyl cellulose, hydroxyethyl cellulose, hydroxypropyl methyl cellulose, methyl cellulose, ethyl cellulose, cellulose acetate, cellulose acetate phthalate, cellulose acetate trimellitate, hydroxypropylmethyl cellulose phthalate, hydroxypropylcellulose phthalate, cellulose hexahydrophthalate, cellulose acetate hexahydrophthalate, and carboxymethylcellulose sodium; acrylic acid polymers and copolymers, preferably formed from acrylic acid, methacrylic acid, acrylic acid alkyl esters, methacrylic acid alkyl esters, and the like, e.g. copolymers of acrylic acid, methacrylic acid, methyl acrylate, ethyl acrylate, methyl methacrylate and/or ethyl methacrylate, with a terpolymer of ethyl acrylate, methyl methacrylate and trimethylammonioethyl methacrylate chloride (sold under the tradename Eudragit RS) preferred; vinyl polymers and copolymers such as polyvinyl pyrrolidone, polyvinyl acetate, polyvinylacetate phthalate, vinylacetate crotonic acid copolymer, and ethylene-vinyl acetate copolymers; zein; and shellac, ammoniated shellac, shellac-acetyl alcohol, and shellac n-butyl stearate. Fatty compounds for use as a sustained release matrix material include, but are not limited to, waxes generally (e.g., carnauba wax) and glyceryl tristearate.

Transmucosal Compositions and Dosage Forms

Although the present compositions may be administered orally, other modes of administration are suitable as well. For example, transmucosal administration may be advantageously employed. Transmucosal administration is carried out using any type of formulation or dosage unit suitable for application to mucosal tissue. For example, the selected active agent may be administered to the buccal mucosa in an adhesive tablet or patch, sublingually administered by placing a solid dosage form under the tongue, lingually administered by placing a solid dosage form on the tongue, administered nasally as droplets or a nasal spray, administered by inhalation of an aerosol formulation, a non-aerosol liquid formulation, or a dry powder, placed within or near the rectum ("transrectal" formulations), or administered to the urethra as a suppository, ointment, or the like.

Preferred buccal dosage forms will typically comprise a therapeutically effective amount of an active agent and a bioerodible (hydrolyzable) polymeric carrier that may also serve to adhere the dosage form to the buccal mucosa. The buccal dosage unit is fabricated so as to erode over a predetermined time period, wherein drug delivery is provided essentially throughout. The time period is typically in the range of from about 1 hour to about 72 hours. Preferred buccal delivery preferably occurs over a time period of from about 2 hours to about 24 hours. Buccal drug delivery for short term use should preferably occur over a time period of from about 2 hours to about 8 hours, more preferably over a time period of from about 3 hours to about 4 hours. As needed buccal drug delivery preferably will occur over a time period of from about 1 hour to about 12 hours, more preferably from about 2 hours to about 8 hours, most preferably from about 3 hours to about 6 hours. Sustained buccal drug delivery will preferably occur over a time period of from about 6 hours to about 72 hours, more preferably from about 12 hours to about 48 hours, most preferably from about 24 hours to about 48 hours. Buccal drug delivery, as will be appreciated by those skilled in the art, avoids the disadvantages encountered with oral drug administration, e.g., slow absorption, degradation of the active agent by fluids present in the gastrointestinal tract and/or first-pass inactivation in the liver.

The "therapeutically effective amount" of the active agent in the buccal dosage unit will of course depend on the potency of the agent and the intended dosage, which, in turn, is dependent on the particular individual undergoing treatment, the specific indication, and the like. The buccal dosage unit will generally contain from about 1.0 wt. % to about 60 wt. % active agent, preferably on the order of from about 1 wt. % to about 30 wt. % active agent. With regard to the bioerodible (hydrolyzable) polymeric carrier, it will be appreciated that virtually any such carrier can be used, so long as the desired drug release profile is not compromised, and the carrier is compatible with the Cav2.2 subunit calcium channel modulator to be administered and any other components of the buccal dosage unit. Generally, the polymeric carrier comprises a hydrophilic (water-soluble and water-swellable) polymer that adheres to the wet surface of the buccal mucosa. Examples of polymeric carriers useful herein include acrylic acid polymers and co, e.g., those known as "carbomers" (Carbopol®, which may be obtained from B.F. Goodrich, is one such polymer). Other suitable polymers include, but are not limited to: hydrolyzed polyvinylalcohol; polyethylene oxides (e.g., Sentry Polyox® water soluble resins, available from Union Carbide); polyacrylates (e.g., Gantrez®, which may be obtained from GAF); vinyl polymers and copolymers; polyvinylpyrrolidone; dextran; guar gum; pectins; starches; and cellulosic polymers such as hydroxypropyl methylcellulose, (e.g., Methocel®, which may be obtained from the Dow Chemical Company), hydroxypropyl cellulose (e.g., Klucel®, which may also be obtained from Dow), hydroxypropyl cellulose ethers (see, e.g., U.S. Pat. No. 4,704,285 to Alderman), hydroxyethyl cellulose, carboxymethyl cellulose, sodium carboxymethyl cellulose, methyl cellulose, ethyl cellulose, cellulose acetate phthalate, cellulose acetate butyrate, and the like.

Other components may also be incorporated into the buccal dosage forms described herein. The additional components include, but are not limited to, disintegrants, diluents, binders, lubricants, flavoring, colorants, preservatives, and the like. Examples of disintegrants that may be used include, but are not limited to, cross-linked polyvinylpyrrolidones, such as crospovidone (e.g., Polyplasdone® XL, which may be obtained from GAF), cross-linked carboxylic methylcelluloses, such as croscarmelose (e.g., Ac-di-sol®, which may be obtained from FMC), alginic acid, and sodium carboxymethyl starches (e.g., Explotab®, which may be obtained from Edward Medell Co., Inc.), methylcellulose, agar bentonite and alginic acid. Suitable diluents are those which are generally useful in pharmaceutical formulations prepared using compression techniques, e.g., dicalcium phosphate dihydrate (e.g., Di-Tab®, which may be obtained from Stauffer), sugars that have been processed by cocrystallization with dextrin (e.g., co-crystallized sucrose and dextrin such as Di-Pak®, which may be obtained from Amstar), calcium phosphate, cellulose, kaolin, mannitol, sodium chloride, dry starch, powdered sugar and the like. Binders, if used, are those that enhance adhesion. Examples of such binders include, but are not limited to, starch, gelatin and sugars such as sucrose, dextrose, molasses, and lactose. Particularly preferred lubricants are stearates and stearic acid, and an optimal lubricant is magnesium stearate.

Sublingual and lingual dosage forms include tablets, creams, ointments, lozenges, pastes, and any other solid dosage form where the active ingredient is admixed into a disintegrable matrix. The tablet, cream, ointment or paste for sublingual or lingual delivery comprises a therapeutically effective amount of the selected active agent and one or more conventional nontoxic carriers suitable for sublingual or lingual drug administration. The sublingual and lingual dosage forms of the present invention can be manufactured using conventional processes. The sublingual and lingual dosage units are fabricated to disintegrate rapidly. The time period for complete disintegration of the dosage unit is typically in the range of from about 10 seconds to about 30 minutes, and optimally is less than 5 minutes.

Other components may also be incorporated into the sublingual and lingual dosage forms described herein. The additional components include, but are not limited to binders, disintegrants, wetting agents, lubricants, and the like. Examples of binders that may be used include water, ethanol, polyvinylpyrrolidone; starch solution gelatin solution, and the like. Suitable disintegrants include dry starch, calcium carbonate, polyoxyethylene sorbitan fatty acid esters, sodium lauryl sulfate, stearic monoglyceride, lactose, and the like. Wetting agents, if used, include glycerin, starches, and the like. Particularly preferred lubricants are stearates and polyethylene glycol. Additional components that may be incorporated into sublingual and lingual dosage forms are known, or will be apparent, to those skilled in this art (See, e.g., Remington: The Science and Practice of Pharmacy, supra).

For transurethral administration, the formulation comprises a urethral dosage form containing the active agent and one or more selected carriers or excipients, such as water, silicone, waxes, petroleum jelly, polyethylene glycol ("PEG"), propylene glycol ("PG"), liposomes, sugars such as mannitol and lactose, and/or a variety of other materials, with polyethylene glycol and derivatives thereof particularly preferred.

Depending on the particular active agent administered, it may be desirable to incorporate a transurethral permeation enhancer in the urethral dosage form. Examples of suitable transurethral permeation enhancers include dimethylsulfoxide ("DMSO"), dimethyl formamide ("DMF"), N,N-dimethylacetamide ("DMA"), decylmethylsulfoxide ("$C_{10}$MSO"), polyethylene glycol monolaurate ("PEGML"), glycerol monolaurate, lecithin, the 1-substituted azacycloheptan-2-ones, particularly 1-n-dodecylcyclazacycloheptan-2-one (available under the trademark Azone® from Nelson Research & Development Co., Irvine, Calif.), SEPA® (available from Macrochem Co., Lexington, Mass.), surfactants as discussed above, including, for example, Tergitol®, Nonoxynol-9® and TWEEN-80®, and lower alkanols such as ethanol.

Transurethral drug administration, as explained in U.S. Pat. Nos. 5,242,391, 5,474,535, 5,686,093 and 5,773,020, can be carried out in a number of different ways using a variety of urethral dosage forms. For example, the drug can be introduced into the urethra from a flexible tube, squeeze bottle, pump or aerosol spray. The drug may also be contained in coatings, pellets or suppositories that are absorbed, melted or bioeroded in the urethra. In certain embodiments, the drug is included in a coating on the exterior surface of a penile insert. It is preferred, although not essential, that the drug be delivered from at least about 3 cm into the urethra, and preferably from at least about 7 cm into the urethra. Generally, delivery from at least about 3 cm to about 8 cm into the urethra will provide effective results in conjunction with the present method.

Urethral suppository formulations containing PEG or a PEG derivative may be conveniently formulated using conventional techniques, e.g., compression molding, heat molding or the like, as will be appreciated by those skilled in the art and as described in the pertinent literature and pharmaceutical texts. (See, e.g., Remington: The Science and Practice of Pharmacy, supra), which discloses typical methods of preparing pharmaceutical compositions in the form of urethral suppositories. The PEG or PEG derivative preferably has a molecular weight in the range of from about 200 to about 2,500 g/mol, more preferably in the range of from about 1,000 to about 2,000 g/mol. Suitable polyethylene glycol derivatives include polyethylene glycol fatty acid esters, for example, polyethylene glycol monostearate, polyethylene glycol sorbitan esters, e.g., polysorbates, and the like. Depending on the particular active agent, it may also be preferred that urethral suppositories contain one or more solubilizing agents effective to increase the solubility of the active agent in the PEG or other transurethral vehicle.

It may be desirable to deliver the active agent in a urethral dosage form that provides for controlled or sustained release of the agent. In such a case, the dosage form comprises a biocompatible, biodegradable material, typically a biodegradable polymer. Examples of such polymers include polyesters, polyalkylcyanoacrylates, polyorthoesters, polyanhydrides, albumin, gelatin and starch. As explained, for example, in PCT Publication No. WO 96/40054, these and other polymers can be used to provide biodegradable microparticles that enable controlled and sustained drug release, in turn minimizing the required dosing frequency.

The urethral dosage form will preferably comprise a suppository that is on the order of from about 2 to about 20 mm in length, preferably from about 5 to about 10 mm in length, and less than about 5 mm in width, preferably less than about 2 mm in width. The weight of the suppository will typically be in the range of from about 1 mg to about 100 mg, preferably in the range of from about 1 mg to about 50 mg. However, it will be appreciated by those skilled in the art that the size of the suppository can and will vary, depending on the potency of the drug, the nature of the formulation, and other factors.

Transurethral drug delivery may involve an "active" delivery mechanism such as iontophoresis, electroporation or phonophoresis. Devices and methods for delivering drugs in this way are well known in the art. Iontophoretically assisted drug delivery is, for example, described in PCT Publication No. WO 96/40054, cited above. Briefly, the active agent is driven through the urethral wall by means of an electric current passed from an external electrode to a second electrode contained within or affixed to a urethral probe.

Preferred transrectal dosage forms include rectal suppositories, creams, ointments, and liquid formulations (enemas). The suppository, cream, ointment or liquid formulation for transrectal delivery comprises a therapeutically effective amount of the selected active agent and one or more conventional nontoxic carriers suitable for transrectal drug administration. The transrectal dosage forms of the present invention can be manufactured using conventional processes. The transrectal dosage unit can be fabricated to disintegrate rapidly or over a period of several hours. The time period for complete disintegration is preferably in the range of from about 10 minutes to about 6 hours, and optimally is less than about 3 hours.

Other components may also be incorporated into the transrectal dosage forms described herein. The additional components include, but are not limited to, stiffening agents, antioxidants, preservatives, and the like. Examples of stiffening agents that may be used include, for example, paraffin, white wax and yellow wax. Preferred antioxidants, if used, include sodium bisulfite and sodium metabisulfite.

Preferred vaginal or perivaginal dosage forms include vaginal suppositories, creams, ointments, liquid formulations, pessaries, tampons, gels, pastes, foams or sprays. The suppository, cream, ointment, liquid formulation, pessary, tampon, gel, paste, foam or spray for vaginal or perivaginal delivery comprises a therapeutically effective amount of the selected active agent and one or more conventional nontoxic carriers suitable for vaginal or perivaginal drug administration. The vaginal or perivaginal forms of the present invention can be manufactured using conventional processes as disclosed in Remington: The Science and Practice of Pharmacy, supra (see also drug formulations as adapted in U.S. Pat. Nos. 6,515,198; 6,500,822; 6,417,186; 6,416,779; 6,376,500; 6,355,641; 6,258,819; 6,172,062; and 6,086,909). The vaginal or perivaginal dosage unit can be fabricated to disintegrate rapidly or over a period of several hours. The time period for complete disintegration is preferably in the range of from about 10 minutes to about 6 hours, and optimally is less than about 3 hours.

Other components may also be incorporated into the vaginal or perivaginal dosage forms described herein. The additional components include, but are not limited to, stiffening agents, antioxidants, preservatives, and the like. Examples of stiffening agents that may be used include, for example, paraffin, white wax and yellow wax. Preferred antioxidants, if used, include sodium bisulfite and sodium metabisulfite.

The active agents may also be administered intranasally or by inhalation. Compositions for intranasal administration are generally liquid formulations for administration as a spray or in the form of drops, although powder formulations for intranasal administration, e.g., insufflations, are also known, as are nasal gels, creams, pastes or ointments. For liquid formulations, the active agent can be formulated into a solution, e.g., water or isotonic saline, buffered or unbuffered, or as a suspension. Preferably, such solutions or suspensions are isotonic relative to nasal secretions and of about the same pH, ranging e.g., from about pH 4.0 to about pH 7.4 or, from about pH 6.0 to about pH 7.0. Buffers should be physiologically compatible and include, simply by way of example, phosphate buffers. Furthermore, various devices are available in the art for the generation of drops, droplets and sprays, including droppers, squeeze bottles, and manually and electrically powered intranasal pump dispensers. Active agent containing intranasal carriers may also include nasal gels, creams, pastes or ointments with a viscosity of, e.g., from about 10 to about 6500 cps, or greater, depending on the desired sustained contact with the nasal mucosal surfaces. Such carrier viscous formulations may be based upon, simply by way of example, alkylcelluloses and/or other biocompatible carriers of high viscosity well known to the art (see e.g., Remington: The Science and Practice of Pharmacy, supra). Other ingredients, such as art known preservatives, colorants, lubricating or viscous mineral or vegetable oils, perfumes, natural or synthetic plant extracts such as aromatic oils, and humectants and viscosity enhancers such as, e.g., glycerol, can also be included to provide additional viscosity, moisture retention and a pleasant texture and odor for the formulation. Formulations for inhalation may be prepared as an aerosol, either a solution aerosol in which the active agent is solubilized in a carrier (e.g., propellant) or a dispersion aerosol in which the active agent is suspended or dispersed throughout a carrier and an optional solvent. Non-aerosol formulations for inhalation may take the form of a liquid, typically an aqueous suspension, although aqueous solutions may be used as well. In such a case, the carrier is typically a sodium chloride solution having a concentration such that the formulation is isotonic relative to normal body fluid. In addition to the carrier, the liquid formulations may contain water and/or excipients including an antimicrobial preservative (e.g., benzalkonium chloride, benzethonium chloride, chlorobutanol, phenylethyl alcohol, thimerosal and combinations thereof), a buffering agent (e.g., citric acid, potassium metaphosphate, potassium phosphate, sodium acetate, sodium citrate, and combinations thereof), a surfactant (e.g., polysorbate 80, sodium lauryl sulfate, sorbitan monopalmitate and combinations thereof), and/or a suspending agent (e.g., agar, bentonite, microcrystalline cellulose, sodium carboxymethylcellulose, hydroxypropyl methylcellulose, tragacanth, veegum and combinations thereof). Non-aerosol formulations for inhalation may also comprise dry powder formulations, particularly insufflations in which the powder has an average particle size of from about 0.1 μm to about 50 μm, preferably from about 1 μm to about 25 μm.

Topical Formulations

Topical formulations may be in any form suitable for application to the body surface, and may comprise, for example, an ointment, cream, gel, lotion, solution, paste or the like, and/or may be prepared so as to contain liposomes, micelles, and/or microspheres. Preferred topical formulations herein are ointments, creams and gels.

Ointments, as is well known in the art of pharmaceutical formulation, are semisolid preparations that are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency or the like. As with other carriers or vehicles, an ointment base should be inert, stable, nonirritating and nonsensitizing. As explained in Remington: The Science and Practice of Pharmacy, supra, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight (See, e.g., Remington: The Science and Practice of Pharmacy, supra).

Creams, as also well known in the art, are viscous liquids or semisolid emulsions, either oil-in-water or water-in-oil. Cream bases are water-washable, and contain an oil phase, an emulsifier and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic or amphoteric surfactant.

As will be appreciated by those working in the field of pharmaceutical formulation, gels-are semisolid, suspension-type systems. Single-phase gels contain organic macromolecules distributed substantially uniformly throughout the carrier liquid, which is typically aqueous, but also, preferably, contain an alcohol and, optionally, an oil. Preferred "organic macromolecules," i.e., gelling agents, are crosslinked acrylic acid polymers such as the "carbomer" family of polymers, e.g., carboxypolyalkylenes that may be obtained commercially under the Carbopol® trademark. Also preferred are hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methylcellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

Various additives, known to those skilled in the art, may be included in the topical formulations. For example, solubilizers may be used to solubilize certain active agents. For those drugs having an unusually low rate of permeation through the skin or mucosal tissue, it may be desirable to include a permeation enhancer in the formulation; suitable enhancers are as described elsewhere herein.

Transdermal Administration

The compounds of the invention may also be administered through the skin or mucosal tissue using conventional transdermal drug delivery systems, wherein the agent is contained within a laminated structure (typically referred to as a transdermal "patch") that serves as a drug delivery device to be affixed to the skin. Transdermal drug delivery may involve passive diffusion or it may be facilitated using electrotransport, e.g., iontophoresis. In a typical transdermal "patch," the drug composition is contained in a layer, or "reservoir," underlying an upper backing layer. The laminated structure may contain a single reservoir, or it may contain multiple reservoirs. In one type of patch, referred to as a "monolithic" system, the reservoir is comprised of a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are separate and distinct layers, with the adhesive underlying the reservoir which, in this case, may be either a polymeric matrix as described above, or it may be a liquid or hydrogel reservoir, or may take some other form.

The backing layer in these laminates, which serves as the upper surface of the device, functions as the primary structural element of the laminated structure and provides the device with much of its flexibility. The material selected for the backing material should be selected so that it is substantially impermeable to the active agent and any other materials that are present, the backing is preferably made of a sheet or film of a flexible elastomeric material. Examples of polymers that are suitable for the backing layer include polyethylene, polypropylene, polyesters, and the like.

During storage and prior to use, the laminated structure includes a release liner. Immediately prior to use, this layer is removed from the device to expose the basal surface thereof, either the drug reservoir or a separate contact adhesive layer, so that the system may be affixed to the skin. The release liner should be made from a drug/vehicle impermeable material.

Transdermal drug delivery systems may in addition contain a skin permeation enhancer. That is, because the inherent permeability of the skin to some drugs may be too low to allow therapeutic levels of the drug to pass through a reasonably sized area of unbroken skin, it is necessary to coadminister a skin permeation enhancer with such drugs. Suitable enhancers are well known in the art and include, for example, those enhancers listed above in transmucosal compositions.

Parenteral Administration

Parenteral administration, if used, is generally characterized by injection, including intramuscular, intraperitoneal, intravenous (IV) and subcutaneous injection. Injectable formulations can be prepared in conventional forms, either as liquid solutions or suspensions; solid forms suitable for solution or suspension in liquid prior to injection, or as emulsions. Preferably, sterile injectable suspensions are formulated according to techniques known in the art using suitable dispersing or wetting agents and suspending agents. The sterile injectable formulation may also be a sterile injectable solution or a suspension in a nontoxic parenterally acceptable diluent or solvent. Among the acceptable vehicles and solvents that may be employed are water, Ringer's solution and isotonic sodium chloride solution. In addition, sterile, fixed oils are conventionally employed as a solvent or suspending medium. A more recently revised approach for parenteral administration involves use of a slow release or sustained release system (See, e.g., U.S. Pat. No. 3,710,795).

Intravesical Administration

Intravesical administration, if used, is generally characterized by administration directly into the bladder and may include methods as described elsewhere herein. Other methods of intravesical administration may include those described in U.S. Pat. Nos. 6,207,180 and 6,039,967, as well as other methods that are known to one of skill in the art.

Intrathecal Administration

Intrathecal administration, if used, is generally characterized by administration directly into the intrathecal space (where fluid flows around the spinal cord).

One common system utilized for intrathecal administration is the APT Intrathecal treatment system available from Medtronic, Inc. APT Intrathecal uses a small pump that is surgically placed under the skin of the abdomen to deliver medication directly into the intrathecal space. The medication is delivered through a small tube called a catheter that is also surgically placed. The medication can then be administered directly to cells in the spinal cord involved in conveying sensory and motor signals associated with lower urinary tract disorders.

Another system available from Medtronic that is commonly utilized for intrathecal administration is the is the fully implantable, programmable SynchroMed® Infusion System. The SynchroMed® Infusion System has two parts that are both placed in the body during a surgical procedure: the catheter and the pump. The catheter is a small, soft tube. One end is connected to the catheter port of the pump, and the other end is placed in the intrathecal space. The pump is a round metal device about one inch (2.5 cm) thick, three inches (8.5 cm) in diameter, and weighs about six ounces (205 g) that stores and releases prescribed amounts of medication directly into the intrathecal space. It is made of titanium, a lightweight, medical-grade metal. The reservoir is the space inside the pump that holds the medication. The fill port is a raised center portion of the pump through which the pump is refilled. The doctor or a nurse inserts a needle through the patient's skin and through the fill port to fill the pump. Some pumps have a side catheter access port that allows the doctor to inject other medications or sterile solutions directly into the catheter, bypassing the pump.

The SynchroMed® pump automatically delivers a controlled amount of medication through the catheter to the intrathecal space around the spinal cord, where it is most effective. The exact dosage, rate and timing prescribed by the doctor are entered in the pump using a programmer, an external computer-like device that controls the pump's memory. Information about the patient's prescription is stored in the pump's memory. The doctor can easily review this information by using the programmer. The programmer communicates with the pump by radio signals that allow the doctor to tell how the pump is operating at any given time. The doctor also can use the programmer to change your medication dosage.

Methods of intrathecal administration may include those described above available from Medtronic, as well as other methods that are known to one of skill in the art.

Additional Dosage Formulations and Drug Delivery Systems

As compared with traditional drug delivery approaches, some controlled release technologies rely upon the modification of both macromolecules and synthetic small molecules to allow them to be actively instead of passively absorbed into the body. For example, XenoPort Inc. utilizes technology that takes existing molecules and re-engineers them to create new chemical entities (unique molecules) that have improved pharmacologic properties to either: 1) lengthen the short half-life of a drug; 2) overcome poor absorption; and/or 3) deal with poor drug distribution to target tissues. Techniques to lengthen the short half-life of a drug include the use of pro-drugs with slow cleavage rates to release drugs over time or that engage transporters in small and large intestines to allow the use of oral sustained delivery systems, as well as drugs that engage active transport systems. Examples of such controlled release formulations, tablets, dosage forms, and drug delivery systems, and that are suitable for use with the present invention, are described in the following published US and PCT patent applications assigned to Xenoport Inc.: US20030158254; US20030158089; US20030017964; US2003130246; WO02100172; WO02100392; WO02100347; WO02100344; WO0242414; WO0228881; WO0228882; WO0244324; WO0232376; WO0228883; and WO0228411. Some other controlled release technologies rely upon methods that promote or enhance gastric retention, such as those developed by Depomed Inc. Because many drugs are best absorbed in the stomach and upper portions of the small intestine, Depomed has developed tablets that swell in the stomach during the postprandial or fed mode so that they are treated like undigested food. These tablets therefore sit safely and neutrally in the stomach for 6, 8, or more hours and deliver drug at a desired rate and time to upper gastrointestinal sites. Specific technologies in this area include: 1) tablets that slowly erode in gastric fluids to deliver drugs at almost a constant rate (particularly useful for highly insoluble drugs); 2) bi-layer tablets that combine drugs with different characteristics into a single table (such as a highly insoluble drug in an erosion layer and a soluble drug in a diffusion layer for sustained release of both); and 3) combination tablets that can either deliver drugs simultaneously or in sequence over a desired period of time (including an initial burst of a fast acting drug followed by slow and sustained delivery of another drug). Examples of such controlled release formulations that are suitable for use with the present invention and that rely upon gastric retention during the postprandial or fed mode, include tablets, dosage forms, and drug delivery systems in the following US patents assigned to Depomed Inc.: U.S. Pat. Nos. 6,488,962; 6,451,808; 6,340,475; 5,972,389; 5,582,837; and 5,007,790. Examples of such controlled release formulations that are suitable for use with the present invention and that rely upon gastric retention during the postprandial or fed mode, include tablets, dosage forms, and drug delivery systems in the following published US and PCT patent applications assigned to Depomed Inc.: US20030147952; US20030104062; US20030104053; US20030104052; US20030091630; US20030044466; US20030039688; US20020051820; WO0335040; WO0335039; WO0156544; WO0132217; WO9855107; WO9747285; and WO9318755.

Other controlled release systems include those developed by ALZA Corporation based upon: 1) osmotic technology for oral delivery; 2) transdermal delivery via patches; 3) liposomal delivery via intravenous injection; 4) osmotic technology for long-term delivery via implants; and 5) depot technology designed to deliver agents for periods of days to a month. ALZA oral delivery systems include those that employ osmosis to provide precise, controlled drug delivery for up to 24 hours for both poorly soluble and highly soluble drugs, as well as those that deliver high drug doses meeting high drug loading requirements. ALZA controlled transdermal delivery systems provide drug delivery through intact skin for as long as one week with a single application to improve drug absorption and deliver constant amounts of drug into the bloodstream over time. ALZA liposomal delivery systems involve lipid nanoparticles that evade recognition by the immune system because of their unique polyethylene glycol (PEG) coating, allowing the precise delivery of drugs to disease-specific areas of the body. ALZA also has developed osmotically driven systems to enable the continuous delivery of small drugs, peptides, proteins, DNA and other bioactive macromolecules for up to one year for systemic or tissue-specific therapy. Finally, ALZA depot injection therapy is designed to deliver biopharmaceutical agents and small molecules for periods of days to a month using a nonaqueous polymer solution for the stabilization of macromolecules and a unique delivery profile.

Examples of controlled release formulations, tablets, dosage forms, and drug delivery systems that are suitable for use with the present invention are described in the following US patents assigned to ALZA Corporation: U.S. Pat. Nos. 4,367,741; 4,402,695; 4,418,038; 4,434,153; 4,439,199; 4,450,198; 4,455,142; 4,455,144; 4,484,923; 4,486,193; 4,489,197; 4,511,353; 4,519,801; 4,526,578; 4,526,933; 4,534,757; 4,553,973; 4,559,222; 4,564,364; 4,578,075; 4,588,580; 4,610,686; 4,618,487; 4,627,851; 4,629,449; 4,642,233; 4,649,043; 4,650,484; 4,659,558; 4,661,105; 4,662,880; 4,675,174; 4,681,583; 4,684,524; 4,692,336; 4,693,895; 4,704,119; 4,705,515; 4,717,566; 4,721,613; 4,723,957; 4,725,272; 4,728,498; 4,743,248; 4,747,847; 4,751,071; 4,753,802; 4,755,180; 4,756,314; 4,764,380; 4,773,907; 4,777,049; 4,781,924; 4,786,503; 4,788,062; 4,810,502; 4,812,313; 4,816,258; 4,824,675; 4,834,979; 4,837,027; 4,842,867; 4,846,826; 4,847,093; 4,849,226; 4,851,229; 4,851,231; 4,851,232; 4,853,229; 4,857,330; 4,859,470; 4,863,456; 4,863,744; 4,865,598; 4,867,969; 4,871,548; 4,872,873; 4,874,388; 4,876,093; 4,892,778; 4,902,514; 4,904,474; 4,913,903; 4,915,949; 4,915,952; 4,917,895; 4,931,285; 4,946,685; 4,948,592; 4,954,344; 4,957,494; 4,960,416; 4,961,931; 4,961,932; 4,963,141; 4,966,769; 4,971,790; 4,976,966; 4,986,987; 5,006,346; 5,017,381; 5,019,397; 5,023,076; 5,023,088; 5,024,842; 5,028,434; 5,030,454; 5,071,656; 5,077,054; 5,082,668; 5,104,390; 5,110,597; 5,122,128; 5,125,894; 5,141,750; 5,141,752; 5,156,850; 5,160,743; 5,160,744; 5,169,382; 5,171,576; 5,176,665; 5,185,158; 5,190,765; 5,198,223; 5,198,229; 5,200,195; 5,200,196; 5,204,116; 5,208,037; 5,209,746; 5,221,254; 5,221,278; 5,229,133; 5,232,438; 5,232,705; 5,236,689; 5,236,714; 5,240,713; 5,246,710; 5,246,711; 5,252,338; 5,254,349; 5,266,332; 5,273,752; 5,284,660; 5,286,491; 5,308,348; 5,318,558; 5,320,850; 5,322,502; 5,326,571; 5,330,762; 5,338,550; 5,340,590; 5,342,623; 5,344,656; 5,348,746; 5,358,721; 5,364,630; 5,376,377; 5,391,381; 5,402,777; 5,403,275; 5,411,740; 5,417,675; 5,417,676; 5,417,682; 5,423,739; 5,424,289; 5,431,919; 5,443,442; 5,443,459; 5,443,461; 5,456,679; 5,460,826; 5,462,741; 5,462,745; 5,489,281; 5,499,979; 5,500,222; 5,512,293; 5,512,299; 5,529,787; 5,531,736; 5,532,003; 5,533,971; 5,534,263; 5,540,912; 5,543,156; 5,571,525; 5,573,503; 5,591,124; 5,593,695; 5,595,759; 5,603,954; 5,607,696; 5,609,885; 5,614,211; 5,614,578; 5,620,705; 5,620,708; 5,622,530; 5,622,944; 5,633,011; 5,639,477; 5,660,861; 5,667,804; 5,667,805; 5,674,895; 5,688,518; 5,698,224; 5,702,725; 5,702,727; 5,707,663; 5,713,852; 5,718,700; 5,736,580; 5,770,227; 5,780,058; 5,783,213; 5,785,994; 5,795,591; 5,811,465; 5,817,624; 5,824,340; 5,830,501; 5,830,502; 5,840,754; 5,858,407; 5,861,439; 5,863,558; 5,876,750; 5,883,135; 5,897,878; 5,904,934; 5,904,935; 5,906,832; 5,912,268; 5,914,131; 5,916,582; 5,932,547; 5,938,654; 5,941,844; 5,955,103; 5,972,369; 5,972,370; 5,972,379; 5,980,943; 5,981,489; 5,983,130; 5,989,590; 5,995,869; 5,997,902; 6,001,390; 6,004,309; 6,004,578; 6,008,187; 6,020,000; 6,034,101; 6,036,973; 6,039,977; 6,057,374; 6,066,619; 6,068,850; 6,077,538; 6,083,190; 6,096,339; 6,106,845; 6,110,499; 6,120,798; 6,120,803; 6,124,261; 6,130,200; 6,146,662; 6,153,678; 6,174,547; 6,183,466; 6,203,817; 6,210,712; 6,210,713; 6,224,907; 6,235,712; 6,245,357; 6,262,115; 6,264,990; 6,267,984; 6,287,598; 6,289,241; 6,331,311; 6,333,050; 6,342,249; 6,346,270; 6,365,183; 6,368,626; 6,387,403; 6,419,952; 6,440,457; 6,468,961; 6,491,683; 6,512,010; 6,514,530; 6,534,089; 6,544,252; 6,548,083; 6,551,613; 6,572,879; and 6,596,314.

Other examples of controlled release formulations, tablets, dosage forms, and drug delivery systems that are suitable for use with the present invention are described in the following published US patent application and PCT applications assigned to ALZA Corporation: U.S. Pat. No. 20010051183; WO0004886; WO0013663; WO0013674; WO0025753; WO0025790; WO0035419; WO0038650; WO0040218; WO0045790; WO0066126; WO0074650; WO0119337; WO019352; WO0121211; WO0137815; WO0141742; WO0143721; WO0156543; WO03041684; WO03041685; WO03041757; WO03045352; WO03051341; WO03053400; WO03053401; WO9000416; WO9004965; WO9113613; WO9116884; WO9204011; WO9211843; WO9212692; WO9213521; WO9217239; WO9218102; WO9300071; WO9305843; WO9306819; WO9314813; WO9319739; WO9320127; WO9320134; WO9407562; WO9408572; WO9416699; WO9421262; WO9427587; WO9427589; WO9503823; WO9519174; WO9529665; WO9600065; WO9613248; WO9625922; WO9637202; WO9640049; WO9640050; WO9640139; WO9640364; WO9640365; WO9703634; WO9800158; WO9802169; WO9814168; WO9816250; WO9817315; WO9827962; WO9827963; WO9843611; WO9907342; WO9912526; WO9912527; WO9918159; WO9929297; WO9929348; WO9932096; WO9932153; WO9948494; WO9956730; WO9958115; and WO9962496.

Another drug delivery technology suitable for use in the present invention is that disclosed by DepoMed, Inc. in U.S. Pat. No. 6,682,759, which discloses a method for manufacturing a pharmaceutical tablet for oral administration combining both immediate-release and prolonged-release modes of drug delivery. The tablet according to the method comprises a prolonged-release drug core and an immediate-release drug coating or layer, which can be insoluble or sparingly soluble in water. The method limits the drug particle diameter in the immediate-release coating or layer to 10 microns or less. The coating or layer is either the particles themselves, applied as an aqueous suspension, or a solid composition that contains the drug particles incorporated in a solid material that disintegrates rapidly in gastric fluid.

Andrx Corporation has also developed drug delivery technology suitable for use in the present invention that includes: 1) a pelletized pulsatile delivery system ("PPDS"); 2) a single composition osmotic tablet system ("SCOT"); 3) a solubility modulating hydrogel system ("SMHS"); 4) a delayed pulsatile hydrogel system ("DPHS"); 5) a stabilized pellet delivery system ("SPDS"); 6) a granulated modulating hydrogel system ("GMHS"); 7) a pelletized tablet system ("PELTAB"); 8) a porous tablet system ("PORTAB"); and 9) a stabilized tablet delivery system ("STDS"). PPDS uses pellets that are coated with specific polymers and agents to control the release rate of the microencapsulated drug and is designed for use with drugs that require a pulsed release. SCOT utilizes various osmotic modulating agents as well as polymer coatings to provide a zero-order drug release. SMHS utilizes a hydrogel-based dosage system that avoids the "initial burst effect" commonly observed with other sustained-release hydrogel formulations and that provides for sustained release without the need to use special coatings or structures that add to the cost of manufacturing. DPHS is designed for use with hydrogel matrix products characterized by an initial zero-order drug release followed by a rapid release that is achieved by the blending of selected hydrogel polymers to achieve a delayed pulse. SPDS incorporates a pellet core of drug and protective polymer outer layer, and is designed specifically for unstable drugs, while GMHS incorporates hydrogel and binding polymers with the drug and forms granules that are pressed into tablet form. PELTAB provides controlled release by using a water insoluble polymer to coat discrete drug crystals or pellets to enable them to resist the action of fluids in the gastrointestinal tract, and these coated pellets are then compressed into tablets. PORTAB provides controlled release by incorporating an osmotic core with a continuous polymer coating and a water soluble component that expands the core and creates microporous channels through which drug is released. Finally, STDS includes a dual layer coating technique that avoids the need to use a coating layer to separate the enteric coating layer from the omeprazole core.

Examples of controlled release formulations, tablets, dosage forms, and drug delivery systems that are suitable for use with the present invention are described in the following US patents assigned to Andrx Corporation: U.S. Pat. Nos. 5,397,574; 5,419,917; 5,458,887; 5,458,888; 5,472,708; 5,508,040; 5,558,879; 5,567,441; 5,654,005; 5,728,402; 5,736,159; 5,830,503; 5,834,023; 5,837,379; 5,916,595; 5,922,352; 6,099,859; 6,099,862; 6,103,263; 6,106,862; 6,156,342; 6,177,102; 6,197,347; 6,210,716; 6,238,703; 6,270,805; 6,284,275; 6,485,748; 6,495,162; 6,524,620; 6,544,556; 6,589,553; 6,602,522; and 6,610,326.

Examples of controlled release formulations, tablets, dosage forms, and drug delivery systems that are suitable for use with the present invention are described in the following published US and PCT patent applications assigned to Andrx Corporation: US20010024659; US20020115718; US20020156066; WO0004883; WO0009091; WO0012097; WO0027370; WO0050010; WO0132161; WO0134123; WO0236077; WO0236100; WO02062299; WO02062824; WO02065991; WO02069888; WO02074285; WO03000177; WO9521607; WO9629992; WO9633700; WO9640080; WO9748386; WO9833488; WO9833489; WO9930692; WO9947125; and WO9961005.

Some other examples of drug delivery approaches focus on non-oral drug delivery, providing parenteral, transmucosal, and topical delivery of proteins, peptides, and small molecules. For example, the Atrigel® drug delivery system marketed by Atrix Laboratories Inc. comprises biodegradable polymers, similar to those used in biodegradable sutures, dissolved in biocompatible carriers. These pharmaceuticals may be blended into a liquid delivery system at the time of manufacturing or, depending upon the product, may be added later by a physician at the time of use. Injection of the liquid product subcutaneously or intramuscularly through a small gauge needle, or placement into accessible tissue sites through a cannula, causes displacement of the carrier with water in the tissue fluids, and a subsequent precipitate to form from the polymer into a solid film or implant. The drug encapsulated within the implant is then released in a controlled manner as the polymer matrix biodegrades over a period ranging from days to months. Examples of such drug delivery systems include Atrix's Eligard®, Atridox®/Doxirobe®, Atrisorb® FreeFlow™/Atrisorb®-D FreeFlow, bone growth products, and others as described in the following published US and PCT patent applications assigned to Atrix Laboratories Inc.: U.S. Pat. Nos. RE37950; 6,630,155; 6,566,144; 6,610,252; 6,565,874; 6,528,080; 6,461,631; 6,395,293; 6,261,583; 6,143,314; 6,120,789; 6,071,530; 5,990,194; 5,945,115; 5,888,533; 5,792,469; 5,780,044; 5,759,563; 5,744,153; 5,739,176 5,736,152; 5,733,950; 5,702,716; 5,681,873; 5,660,849; 5,599,552; 5,487,897; 5,368,859; 5,340,849; 5,324,519; 5,278,202; 5,278,201; US20020114737, US20030195489; US20030133964; US 20010042317; US20020090398; US20020001608; and US2001042317.

Atrix Laboratories Inc. also markets technology for the non-oral transmucosal delivery of drugs over a time period from minutes to hours. For example, Atrix's BEMA™ (Bioerodible Muco-Adhesive Disc) drug delivery system comprises pre-formed bioerodible discs for local or systemic delivery. Examples of such drug delivery systems include those as described in U.S. Pat. No. 6,245,345.

Other drug delivery systems marketed by Atrix Laboratories Inc. focus on topical drug delivery. For example, SMP™ (Solvent Particle System) allows the topical delivery of highly water-insoluble drugs. This product allows for a controlled amount of a dissolved drug to permeate the epidermal layer of the skin by combining the dissolved drug with a microparticle suspension of the drug. The SMP™ system works in stages whereby: 1) the product is applied to the skin surface; 2) the product near follicles concentrates at the skin pore; 3) the drug readily partitions into skin oils; and 4) the drug diffuses throughout the area. By contrast, MCA® (Mucocutaneous Absorption System) is a water-resistant topical gel providing sustained drug delivery. MCA® forms a tenacious film for either wet or dry surfaces where: 1) the product is applied to the skin or mucosal surface; 2) the product forms a tenacious moisture-resistant film; and 3) the adhered film provides sustained release of drug for a period from hours to days. Yet another product, BCP (Biocompatible Polymer System) provides a non-cytotoxic gel or liquid that is applied as a protective film for wound healing. Examples of these systems include Orajel®-Ultra Mouth Sore Medicine as well as those as described in the following published US patents and applications assigned to Atrix Laboratories Inc.: U.S. Pat.

Nos. 6,537,565; 6,432,415; 6,355,657; 5,962,006; 5,725,491; 5,722,950; 5,717,030; 5,707,647; 5,632,727; and US20010033853.

Dosage and Administration

The concentration of the active agent in any of the aforementioned dosage forms and compositions can vary a great deal, and will depend on a variety of factors, including the type of composition or dosage form, the corresponding mode of administration, the nature and activity of the specific active agent, and the intended drug release profile. Preferred dosage forms contain a unit dose of active agent, i.e., a single therapeutically effective dose. For creams, ointments, etc., a "unit dose" requires an active agent concentration that provides a unit dose in a specified quantity of the formulation to be applied. The unit dose of any particular active agent will depend, of course, on the active agent and on the mode of administration.

For a Cav2.2 subunit calcium channel modulator, the unit dose for oral, intravesical, transmucosal, topical, transdermal, and parenteral administration will be in the range of from about 1 ng to about 10,000 mg, typically in the range of from about 100 ng to about 5,000 mg. Alternatively, for a Cav2.2 subunit calcium channel modulator, the unit dose for oral, intravesical, transmucosal, topical, transdermal, and parenteral administration will be greater than about 1 ng, about 5 ng, about 10 ng, about 20 ng, about 30 ng, about 40 ng, about 50 ng, about 100 ng, about 200 ng, about 300 ng, about 400 ng, about 500 ng, about 1 µg, about 5 µg, about 10 µg, about 20 µg, about 30 µg, about 40 µg, about 50 µg, about 100 µg, about 200 µg, about 300 µg, about 400 µg, about 500 µg, about 1 mg, about 5 mg, about 10 mg, about 20 mg, about 30 mg, about 40 mg, about 50 mg, about 100 mg, about 200 mg, about 300 mg, about 400 mg, about 500 mg, about 1,000 mg, about 1,500 mg, about 2,000 mg, about 2,500 mg, about 3,000 mg, about 3,500 mg, about 4,000 mg, about 4,500 mg, about 5,000 mg, about 5,500 mg, about 6,000 mg, about 6,500 mg, about 7,000 mg, about 7,500 mg, about 8,000 mg, about 8,500 mg, about 9,000 mg, or about 9,500 mg. Those of ordinary skill in the art of pharmaceutical formulation can readily deduce suitable unit doses for a Cav2.2 subunit calcium channel modulator, as well as suitable unit doses for other types of agents that may be incorporated into a dosage form of the invention.

For a Cav2.2 subunit calcium channel modulator, the unit dose for intrathecal administration will be in the range of from about 1 fg to about 1 mg, typically in the range of from about 100 fg to about 1 ng. Alternatively, for a Cav2.2 subunit calcium channel modulator, the unit dose for oral administration will be greater than about 1 fg, about 5 fg, about 10 fg, about 20 fg, about 30 fg, about 40 fg, about 50 fg, about 100 fg, about 200 fg, about 300 fg, about 400 fg, about 500 fg, about 1 pg, about 5 pg, about 10 pg, about 20 pg, about 30 pg, about 40 pg, about 50 pg, about 100 pg, about 200 pg, about 300 pg, about 400 pg, about 500 pg, about 1 ng, about 5 ng, about 10 ng, about 20 ng, about 30 ng, about 40 ng, about 50 ng, about 100 ng, about 200 ng, about 300 ng, about 400 ng, about 500 ng, about 1 µg, about 5 µg, about 10 µg, about 20 µg, about 30 µg, about 40 µg, about 50 µg, about 100 µg, about 200 µg, about 300 µg, about 400 µg, or about 500 µg. Those of ordinary skill in the art of pharmaceutical formulation can readily deduce suitable unit doses for a Cav2.2 subunit calcium channel modulator, as well as suitable unit doses for other types of agents that may be incorporated into a dosage form of the invention.

A therapeutically effective amount of a particular active agent administered to a given individual will, of course, be dependent on a number of factors, including the concentration of the specific active agent, composition or dosage form, the selected mode of administration, the age and general condition of the individual being treated, the severity of the individual's condition, and other factors known to the prescribing physician.

In a preferred embodiment, drug administration is on an as-needed basis, and does not involve chronic drug administration. With an immediate release dosage form, as-needed administration may involve drug administration immediately prior to commencement of an activity wherein suppression of the symptoms of overactive bladder would be desirable, but will generally be in the range of from about 0 minutes to about 10 hours prior to such an activity, preferably in the range of from about 0 minutes to about 5 hours prior to such an activity, most preferably in the range of from about 0 minutes to about 3 hours prior to such an activity. With a sustained release dosage form, a single dose can provide therapeutic efficacy over an extended time period in the range of from about 1 hour to about 72 hours, typically in the range of from about 8 hours to about 48 hours, depending on the formulation. That is, the release period may be varied by the selection and relative quantity of particular sustained release polymers. If necessary, however, drug administration may be carried out within the context of an ongoing dosage regimen, i.e., on a weekly basis, twice weekly, daily, etc.

Packaged Kits

In another embodiment, a packaged kit is provided that contains the pharmaceutical formulation to be administered, i.e., a pharmaceutical formulation containing a therapeutically effective amount of a selected active agent for the treatment of painful and non-painful lower urinary tract disorders, and the related genitourinary tract disorders vulvodynia and vulvar vestibulitis, in normal and spinal cord injured patients, a container, preferably sealed, for housing the formulation during storage and prior to use, and instructions for carrying out drug administration in a manner effective to treat painful and non-painful lower urinary tract disorders, and the related genitourinary tract disorders vulvodynia and vulvar vestibulitis, in normal and spinal cord injured patients. The instructions will typically be written instructions on a package insert and/or on a label. Depending on the type of formulation and the intended mode of administration, the kit may also include a device for administering the formulation. The formulation may be any suitable formulation as described herein. For example, the formulation may be an oral dosage form containing a unit dosage of a selected active agent.

The kit may contain multiple formulations of different dosages of the same agent. The kit may also contain multiple formulations of different active agents. The kit may contain formulations suitable for sequential, separate and/or simultaneous use in the treatment of lower urinary tract disorders, and instructions for carrying out drug administration where the formulations are administered sequentially, separately and/or simultaneously in the treatment of lower urinary tract disorders.

The parts of the kit may be independently held in one or more containers—such as bottles, syringes, plates, wells, blister packs, or any other type of pharmaceutical packaging.

Insurance Claims

In general, the processing of an insurance claim for the coverage of a given medical treatment or drug therapy involves notification of the insurance company, or any other entity, that has issued the insurance policy against which the claim is being filed, that the medical treatment or drug therapy will be performed. A determination is then made as to whether the medical treatment or drug therapy that will be performed is covered under the terms of the policy. If covered, the claim is then processed, which can include payment, reimbursement, or application against a deductable.

The present invention encompasses a method for processing an insurance claim under an insurance policy for an active agent or pharmaceutically acceptable salts, esters, amides, prodrugs, or active metabolites thereof used in the treatment of lower urinary tract disorders, wherein said active agent or pharmaceutically acceptable salts, esters, amides, prodrugs, or active metabolites thereof are administered sequentially or concurrently in different compositions. This method comprises: 1) receiving notification that treatment using said active agent or pharmaceutically acceptable salts, esters, amides, prodrugs or active metabolites thereof will be performed or notification of a prescription; 2) determining whether said treatment using said active agent or pharmaceutically acceptable salts, esters, amides, prodrugs or active metabolites is covered under said insurance policy; and 3) processing said claim for treatment of said lower urinary tract disorders using said active agent or pharmaceutically acceptable salts, esters, amides, prodrugs, or active metabolites thereof, including payment, reimbursement, or application against a deductable. This method also encompasses the processing of claims for more than one active agent, whether they have been prescribed separately or concurrently for the treatment of lower urinary tract disorders.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended embodiments. Although specific terms are employed herein, they are used in a generic and descriptive sense only and not for purposes of limitation.

EXAMPLES

Methods For Treating Lower Urinary Tract Disorders Using Cav2.2 Subunit Calcium Channel Modulators The invention will be further described in the following examples, which do not limit the scope of the invention described in the claims. The following examples illustrate the effects of administration of Cav2.2 subunit calcium channel modulators in models for lower urinary tract disorders, and it is expected that these results will demonstrate the efficacy of Cav2.2 subunit calcium channel modulators for treatment of painful and non-painful lower urinary tract disorders and the related disorders vulvodynia and vulvar vestibulitis in normal and spinal cord injured patients as described herein.

These methods include the use of a well accepted model for urinary tract disorders involving the bladder using intravesically administered acetic acid as described in Sasaki et al. (2002) *J. Urol.* 168: 1259-64. These methods also include the use of a well-accepted model for urinary tract disorders involving examination of calcium channel currents recorded from bladder sensory neurons as described in Yoshimura et al. (2001) *J. Neurophys.* 86: 304-311. Efficacy for treating spinal cord injured patients can be tested using methods as described in Yoshiyama et al. (1999) *Urology* 54: 929-33.

Example 1

Dilute Acetic Acid Model

Objective and Rationale

The objective of the current study was to determine the ability of Cav2.2 subunit calcium channel modulators to reverse the reduction in bladder capacity and shortening of intermicturition interval seen following continuous infusion of dilute acetic acid, a commonly used model of lower urinary tract disorders.

Materials and Methods

Animal Preparation: Female Sprague-Dawley rats (Charles River, 250-300 g, n=5) were anesthetized with urethane (1.2 g/kg) and an intrathecal catheter (PE10) filled with artificial cerebrospinal fluid (aCSF) was inserted through a small incision in the atlanto-occipital membrane and the tip was positioned at the sacral spinal cord (8.5 cm from insertion). The intrathecal catheter was fixed in place and the overlying skin closed with tissue adhesive. A PE50 catheter with a fire-flared tip was inserted into the dome of the bladder through a small cystotomy and secured by ligation for bladder filling and pressure recording. Small diameter (75 µm) stainless steel wires were inserted percutaneously into the external urethral sphincter for electromyography. The abdomen was covered with clear plastic cellophane in order to minimize body fluid loss. Animals were positioned on a heating pad which maintained body temperature at 37 C.

Experimental Design: Following a 60-90 minute control period of normal saline infusion (0.055 ml/min) to collect baseline continuous open cystometric data, the pump was turned off, the bladder was emptied, the pump turned back on, and bladder capacity was estimated by a filling cystometrogram. Bladder infusate was then switched to 0.25% acetic acid in saline and continuous open cystometry was resumed. At 3×20-30 minute intervals, 5 µl of aCSF vehicle was administered intrathecally, and was followed immediately by 7 µl of aCSF in order to clear catheter dead space (total catheter luminal volume is 6 µl). These same volumes and protocol were utilized for all intrathecal drug deliveries. This vehicle challenge was repeated twice for a toal of 3 vehicle controls prior to initiating a cumulative dosing of ω-Conotoxin MVIIA. Additionally, following the third vehicle control, bladder capacity was again estimated as described above. Subsequently, the lowest dose of ω-Conotoxin MVIIA was administered intrathecally, and 20 minutes later bladder capacity was again measured. This process was repeated for each drug dose until the dose-response was finished. ω-Conotoxin MVIIA was administered in doses of 0.03, 0.1, 0.3, 1.0 and 3.0 µg/kg.

Data Analysis

Bladder capacity and intermicturition interval data were analyzed by non-parametric, repeated measures 1-Way ANOVA (Friedman Test) and Dunn's multiple comparison post test. $P<0.05$ was considered significant.

Results and Conclusions

Figure 2:
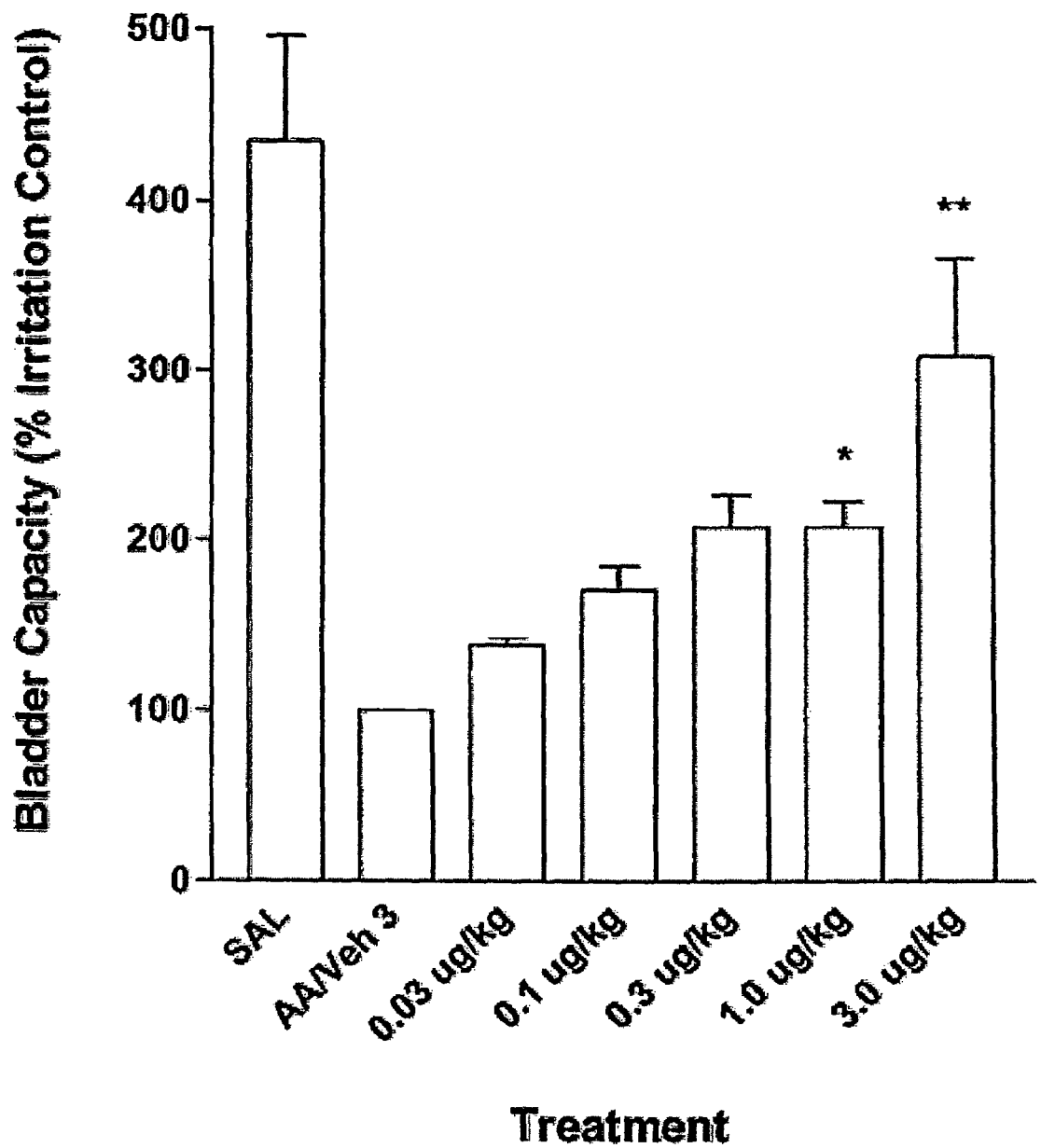
FIG. 2.

Intrathecal vehicle administration had no effect on any measured cystometric parameters. Dilute Acetic Acid resulted in a dramatic 64% reduction in intermicturition interval that was reversed (from 36% to 81% of pre-irritation control values) in a dose-dependent fashion ω-Conotoxin MVIIA (P=0.0010, FIG. 1). The 1.0 and 3.0 µg/kg doses were found to be significantly different than irritation control (AA/Veh 3) by Dunn's multiple comparison test (MCT). Likewise, dilute Acetic Acid resulted in a 77% reduction in directly measured bladder capacity that was also reversed (from 23% to 69% of control values) in a dose-dependent fashion ω-Conotoxin MVIIA (P=0.0005, FIG. 2). The 1.0 and 3.0 μg/kg doses were again found to be significantly different than irritation control by Dunn's MCT (P<0.05 and P<0.01, respectively). These effects were seen with no untoward effects on other micturition parameters, such as voiding efficiency, as determined by both increased intermicturition interval and maintenance of characteristic micturition-associated EUS behavior (not shown).

The ability of Cav2.2 subunit calcium channel modulators to produce a dramatic reversal in acetic acid irritation-induced reduction in bladder capacity and intermicturition interval strongly indicates efficacy in mammalian forms of painful and non-painful lower urinary tract disorders and the related disorders vulvodynia and vulvar vestibulitis in normal and spinal cord injured patients.

Example 2

Bladder Sensory Neuron Calcium Channel Current Model

Objective and Rationale

The objective of the current study was to determine the effect of Cav2.2 subunit calcium channel modulators on the ability to modulate calcium currents in bladder primary afferent neurons, a commonly used model of lower urinary tract disorders.

Methods

Labeling of bladder afferent neurons: Experiments were performed on adult female Sprague-Dawley rats (175-200 g). DRG neurons innervating the urinary bladder were labeled by retrograde axonal transport of the fluorescent dye, Fast Blue (FB) (2% w/v), 12-16 days prior to dissociation. FB dye was injected into the bladder wall of anesthetized animals with a 32 gauge needle at one to three sites around the bladder neck (1-5 μl per site, total volume of 5 μl). The bladder exterior surface was rinsed thoroughly with sterile saline following injections to minimize dye contamination of surrounding tissue.

Neuronal cultures: $L_6$ and $S_1$ DRG neurons were dissociated from dye-injected animals and briefly subjected to collagenase and trypsin digestion. DRG cell bodies were isolated by trituration and then plated on poly-L-lysine coverslips in 24-well plates (0.5 DRGs per well) with 1 ml of plating media (DMEM containing 10% FBS, 25 mM HEPES, 50 ng/ml NGF, 100 U/ml Pen/Strep). DRG neurons were maintained in plating media incubated at 37° C. in 8% $CO_2$. All experimental procedures involving rats were conducted under a protocol approved by an Institutional Animal Care and Use Committee. Small variations in the concentrations of reagents, incubation times, etc. may occur and are expected to give similar results.

Electrophysiology: FITC-labeled isolectin B4 (IB4) (Sigma) solution was added to each coverslip (10 μl/well, final concentration of 10 μg/ml) for five minutes before recording. All recordings were performed within 48 hours after dissociation. Dye-labeled primary afferent bladder neurons were identified using an inverted phase contrast microscope with fluorescence optics. Neurons were selected for recording according to: 1) FB-positive staining, indicating that they were bladder afferent neurons; 2) IB4-negative staining, indicating that they were presumably peptidergic, TrkA-positive neurons; and 3) soma diameter <30 μm, indicating that they were presumably small diameter, C-fiber neurons. Whole cell patch clamp recordings were performed at room temperature. Fire polished patch electrodes had tip resistances of 1-4 MΩ when filled with internal solution. Neurons were superfused at a flow rate of 1 ml/min with external solution.

Whole cell patch clamp experiments were performed using a MultiClamp 700A amplifier (Axon Instruments). Data were acquired, digitized at 5 kHz, and analyzed by pClamp software (Axon Instruments). Leak currents were subtracted by P/4 pulse protocol and series resistance was compensated by 50-70%.

Voltage clamp recordings used external and internal solutions that contained respectively (mM), 155 TEA-Cl, 5 $BaCl_2$, 10 glucose, 5 4-aminopyridine, 10 HEPES adjusted to pH 7.4 with TEA-OH (340 mOsm) and 140 KCl, 1 $CaCl_2$, 2 $MgCl_2$, 9 EGTA, 10 HEPES, 4 Mg ATP, 0.3 GTP (Tris Salt) adjusted to pH 7.4 with KOH (31 OmOsm). All neurons were voltage-clamped at holding potentials of −80 or −60 mV. HVA calcium currents were elicited by depolarizing pulses to 0 mV at low frequency stimulation (10-15 s) and allowed to stabilize prior to compound application. In these experiments, barium was used as the charge carrier through calcium channels. Peak currents were measured for analysis of drug effects.

Omega-conotoxin GVIA was initially dissolved in $H_2O$ before final dilution in the external solution. It was then applied to neurons via bath perfusion.

Results and Conclusions

Figure 3A:
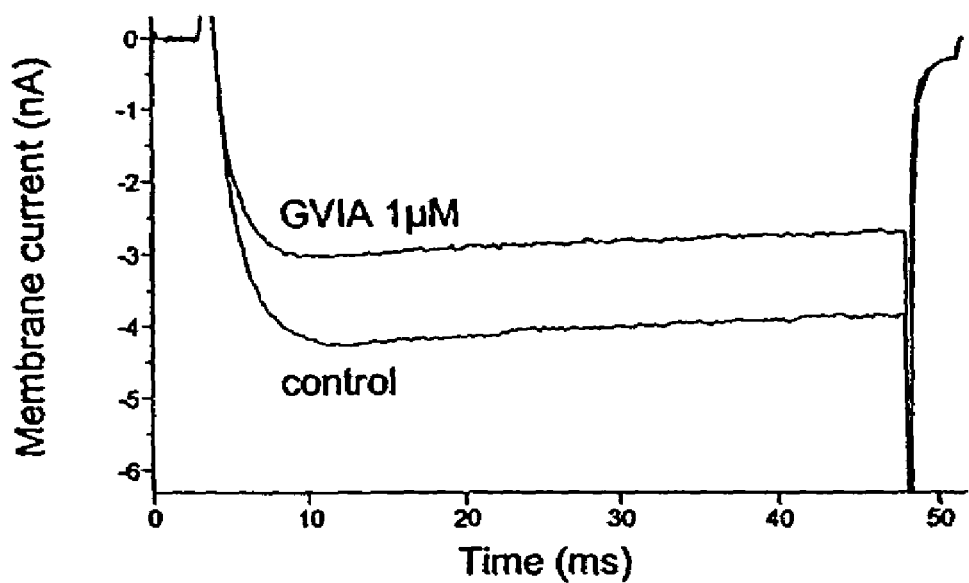
FIG. 3A depicts HVA calcium channel currents in dorsal root ganglion neurons innervating the urinary bladder induced by depolarizing pulses (−80 to 0 mV) before (control) and after application of Omega-conotoxin GVIA.
Figure 3B:
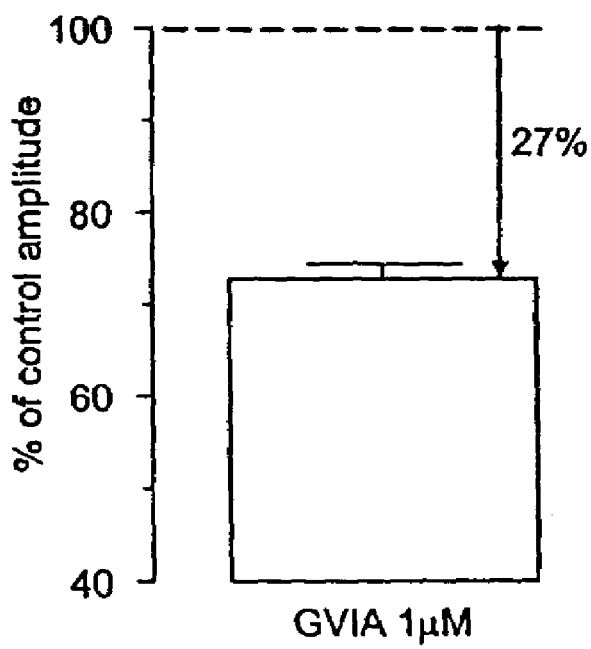
FIG. 3B depicts changes in peak HVA calcium currents in bladder afferents following application of Omega-conotoxin GVIA expressed as percentage of control peak calcium current amplitude.

HVA calcium channel currents were evaluated in voltage clamp recordings using an external solution that suppressed sodium and potassium currents. Only bladder afferent neurons were evaluated in this study. Omega-conotoxin GVIA (1 μM), a selective Cav2.2 calcium channel blocker, inhibited calcium current amplitudes evoked by depolarizing pulses (−80 to 0 mV) to 72.8±1.6% (n=4) of control amplitudes (FIG. 3A,B). This represents the total Cav2.2 component contribution to HVA calcium channels recorded under the present conditions.

The ability of Cav2.2 subunit calcium channel modulators to modulate HVA calcium channel currents in bladder afferent DRG strongly indicates efficacy in mammalian forms of painful and non-painful lower urinary tract disorders and the related disorders vulvodynia and vulvar vestibulitis in normal and spinal cord injured patients.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

What is claimed is:

1. A method for treating overactive bladder which comprises administering to an individual in need thereof a therapeutically effective amount of an active agent wherein said agent is Ziconotide (ω-conotoxin MVIIA) or a pharmaceutically acceptable salt thereof.

2. The method of claim 1, wherein the active agent is contained within a pharmaceutical formulation.

3. The method of claim 2, wherein the pharmaceutical formulation is a unit dosage formulation.

4. The method of claim 1, wherein the active agent is administered on an as-needed basis.

5. The method of claim 1, wherein the active agent is administered prior to commencement of an activity wherein suppression of the symptoms of overactive bladder would be desirable.

6. The method of claim 5, wherein the active agent is administered from about 0 to about 3 hours prior to commencement of an activity wherein suppression of said symptoms would be desirable.

7. The method of claim 2, wherein the formulation is a controlled release dosage formulation.

8. The method of claim 7, wherein the formulation is a delayed release dosage formulation.

9. The method of claim 7, wherein the formulation is a sustained release dosage formulation.

10. The method of claim 9, wherein the sustained release dosage formulation provides drug release over a time period of from about 6 hours to about 8 hours.

11. The method of claim 1, wherein said overactive bladder is OAB Wet.

12. The method of claim 1, wherein said overactive bladder is OAB Dry.

13. The method of claim 2, wherein the pharmaceutical formulation further comprises an additional active agent.

14. The method of claim 13, wherein the additional active agent is ω- conotoxin GVIA or a salt thereof.

* * * * *